US012303380B2

(12) United States Patent
Wiemer et al.

(10) Patent No.: US 12,303,380 B2
(45) Date of Patent: May 20, 2025

(54) COMPENSATING CORNEAL OPACITY

(71) Applicant: Tectus Corporation, Saratoga, CA (US)

(72) Inventors: Michael West Wiemer, San Jose, CA (US); Morrison Ulman, Los Altos, CA (US); Drew Daniel Perkins, Saratoga, CA (US)

(73) Assignee: Tectus Corporation, Saratoga, CA (US)

(*) Notice: Subject to any disclaimer, the term of this patent is extended or adjusted under 35 U.S.C. 154(b) by 970 days.

(21) Appl. No.: 17/235,572

(22) Filed: Apr. 20, 2021

(65) Prior Publication Data

US 2021/0290367 A1    Sep. 23, 2021

Related U.S. Application Data

(63) Continuation of application No. PCT/US2021/023462, filed on Mar. 22, 2021.
(Continued)

(51) Int. Cl.
*A61F 2/16* (2006.01)
*A61B 5/00* (2006.01)
(Continued)

(52) U.S. Cl.
CPC .............. *A61F 2/16* (2013.01); *A61B 5/076* (2013.01); *A61B 5/686* (2013.01); *A61F 9/08* (2013.01);
(Continued)

(58) Field of Classification Search
CPC ......... A61F 2/16; A61F 9/08; G02B 27/0093; G02C 11/10
See application file for complete search history.

(56) References Cited

U.S. PATENT DOCUMENTS 3,996,627 A   12/1976  Deeg
4,470,159 A    9/1984  Peyman
(Continued)

FOREIGN PATENT DOCUMENTS

WO   1996017562 A1   6/1996
WO   2006015315      2/2006
(Continued)

OTHER PUBLICATIONS

Characterization of an Electronic Corneal Prosthesis System, Shim et al., Current Eye Research 2019 {https://doi.org/10.1080/02713683.2019.1708957} 7 pages.
(Continued)

*Primary Examiner* — Bruce E Snow
(74) *Attorney, Agent, or Firm* — Fenwick & West LLP

(57) ABSTRACT

An electronic intraocular device is implantable into the capsular bag of a wearer's eye. In some cases, the intraocular device may include a femtoprojector. The femtoprojector projects images onto the wearer's retina when the electronic intraocular device is implanted in the wearer's eye. Different haptic designs may be used to keep the femtoprojector in position. In some embodiments, an imager is contained in a contact lens worn by the wearer. Images captured by the contact lens imager may be relayed to the intraocular femtoprojector. In some cases, the intraocular device may include an electronic capsular tension ring with a femtoimager. The femtoimager may capture images of the wearer's retina, for example for purposes of monitoring eye health.

15 Claims, 27 Drawing Sheets

Related U.S. Application Data

(60) Provisional application No. 63/149,962, filed on Feb. 16, 2021, provisional application No. 63/064,354, filed on Aug. 11, 2020, provisional application No. 62/993,607, filed on Mar. 23, 2020.

(51) Int. Cl.

| | | |
|---|---|---|
| *A61B 5/07* | (2006.01) | |
| *A61F 9/08* | (2006.01) | |
| *G02B 17/06* | (2006.01) | |
| *G02B 27/00* | (2006.01) | |
| *G02B 27/01* | (2006.01) | |
| *G02C 7/04* | (2006.01) | |
| *G02C 11/00* | (2006.01) | |
| *G06N 20/00* | (2019.01) | |
| *G16H 40/63* | (2018.01) | |
| *H04N 9/31* | (2006.01) | |
| *A61B 3/16* | (2006.01) | |
| *A61B 5/024* | (2006.01) | |
| *A61B 5/145* | (2006.01) | |
| *A61F 2/14* | (2006.01) | |
| *A61F 2/48* | (2006.01) | |
| *H04N 23/50* | (2023.01) | |

(52) U.S. Cl.
CPC ..... *G02B 17/0605* (2013.01); *G02B 27/0093* (2013.01); *G02B 27/0172* (2013.01); *G02C 7/046* (2013.01); *G02C 7/049* (2013.01); *G02C 11/10* (2013.01); *G06N 20/00* (2019.01); *G16H 40/63* (2018.01); *H04N 9/3147* (2013.01); *H04N 9/3173* (2013.01); *A61B 3/16* (2013.01); *A61B 5/0031* (2013.01); *A61B 5/024* (2013.01); *A61B 5/14532* (2013.01); *A61B 5/14542* (2013.01); *A61B 5/7445* (2013.01); *A61F 2/14* (2013.01); *A61F 2002/1681* (2013.01); *A61F 2002/1683* (2013.01); *A61F 2002/1689* (2013.01); *A61F 2/482* (2021.08); *A61F 2250/0002* (2013.01); *G02B 17/0615* (2013.01); *G02B 2027/0138* (2013.01); *G02B 27/017* (2013.01); *G02B 2027/0178* (2013.01); *G02C 2202/10* (2013.01); *H04N 23/555* (2023.01)

(56) References Cited

U.S. PATENT DOCUMENTS

| | | |
|---|---|---|
| 5,597,381 A | 1/1997 | Rizzo, III |
| 5,653,751 A | 8/1997 | Samiy |
| 6,749,631 B1 | 6/2004 | Pietrini |
| 7,001,427 B2 | 2/2006 | Aharoni |
| 7,248,928 B2 | 7/2007 | Yagi |
| 7,727,277 B2 | 6/2010 | Aharoni |
| 7,736,390 B2 | 6/2010 | Aharoni |
| 7,776,087 B2 | 8/2010 | Aharoni |
| 7,918,886 B2 | 4/2011 | Aharoni |
| 7,957,810 B2 | 6/2011 | Greenberg |
| 8,197,539 B2 | 6/2012 | Nasiatka |
| 8,428,740 B2 | 4/2013 | Gefen |
| 8,718,784 B2 | 5/2014 | Gefen |
| 8,956,396 B1 | 2/2015 | Friend |
| 9,192,464 B2 | 11/2015 | Liran |
| 9,192,772 B1 | 11/2015 | Tsukamoto |
| 9,198,753 B2 | 12/2015 | Gefen |
| 9,314,626 B2 | 4/2016 | McDermott |
| 9,331,791 B2 | 5/2016 | Liran |
| 9,370,417 B2 | 6/2016 | Gefen |
| 9,414,907 B2 | 8/2016 | Wortz |
| 9,439,754 B2 | 9/2016 | Wortz |
| 9,474,902 B2 | 10/2016 | Gefen |
| 9,554,890 B2 | 1/2017 | Wortz |
| 9,642,699 B2 | 5/2017 | Wortz |
| 10,076,408 B2 | 9/2018 | Basinger |
| 10,467,992 B2 | 11/2019 | Deering |
| 11,696,853 B2 * | 7/2023 | Saini ................... A61F 9/08 |
| | | 623/6.22 |
| 11,956,414 B2 * | 4/2024 | Freeman ............ G06V 40/193 |
| 2003/0014089 A1 | 1/2003 | Chow |
| 2004/0039401 A1 | 2/2004 | Chow |
| 2004/0054407 A1 | 3/2004 | Tashiro |
| 2004/0078064 A1 | 4/2004 | Suzuki |
| 2005/0090875 A1 | 4/2005 | Palanker |
| 2005/0165409 A1 | 7/2005 | Eckmiller |
| 2005/0168569 A1 | 8/2005 | Igarashi |
| 2006/0116743 A1 | 6/2006 | Gibson |
| 2006/0224212 A1 | 10/2006 | Kennedy |
| 2007/0139613 A1 | 6/2007 | Tanifuji |
| 2009/0190026 A1 | 7/2009 | Chen |
| 2009/0216295 A1 | 8/2009 | Zrenner |
| 2010/0204754 A1 | 8/2010 | Gross |
| 2011/0160853 A1 | 6/2011 | Scholten |
| 2012/0035726 A1 | 2/2012 | Gross |
| 2012/0065704 A1 | 3/2012 | Kavasssery |
| 2012/0194781 A1 | 8/2012 | Agurok |
| 2012/0239126 A1 | 9/2012 | Zhou |
| 2013/0301004 A1 | 11/2013 | Kahn |
| 2014/0046418 A1 | 2/2014 | Williams |
| 2014/0143559 A1 | 5/2014 | Gefen |
| 2015/0342723 A1 | 12/2015 | Abramson |
| 2015/0378176 A1 | 12/2015 | Flitsch |
| 2016/0099046 A1 | 4/2016 | Liran |
| 2016/0220828 A1 | 8/2016 | Yan Poon |
| 2016/0310325 A1 | 10/2016 | Jiao |
| 2017/0368351 A1 | 12/2017 | Liran |
| 2018/0071146 A1 | 3/2018 | Liran |
| 2018/0098696 A1 | 4/2018 | Blaauw |
| 2018/0117329 A1 | 5/2018 | Degtiar |
| 2018/0117330 A1 | 5/2018 | Weinberger |
| 2018/0120568 A1 | 5/2018 | Miller |
| 2018/0153399 A1 | 6/2018 | Fink |
| 2018/0271642 A1 | 9/2018 | Wortz |
| 2018/0335835 A1 | 11/2018 | Lemoff |
| 2018/0353331 A1 | 12/2018 | Saini |
| 2018/0367769 A1 | 12/2018 | Greenberg |
| 2019/0012989 A1 | 1/2019 | Deering |
| 2019/0046798 A1 | 2/2019 | Kindt |
| 2019/0065970 A1 | 2/2019 | Bonutti |
| 2019/0151077 A1 | 5/2019 | Chodosh |
| 2019/0232051 A1 | 8/2019 | Gross |
| 2019/0235276 A1 | 8/2019 | Wiemer |
| 2019/0235283 A1 | 8/2019 | Tuan |
| 2019/0251893 A1 | 8/2019 | Martin |
| 2019/0274822 A1 | 9/2019 | Grant |
| 2019/0369417 A1 | 12/2019 | Kniess |
| 2020/0033637 A1 | 1/2020 | Jamshidi |
| 2020/0038247 A1 | 2/2020 | Liran |

FOREIGN PATENT DOCUMENTS

| | | |
|---|---|---|
| WO | 2014122076 | 8/2014 |
| WO | 2019055477 A2 | 3/2019 |

OTHER PUBLICATIONS

Feasibility of Intraocular Projection for Treatment of Intractable Corneal Opacity, Shim et al., Cornea 2019, 5 pages.

* cited by examiner

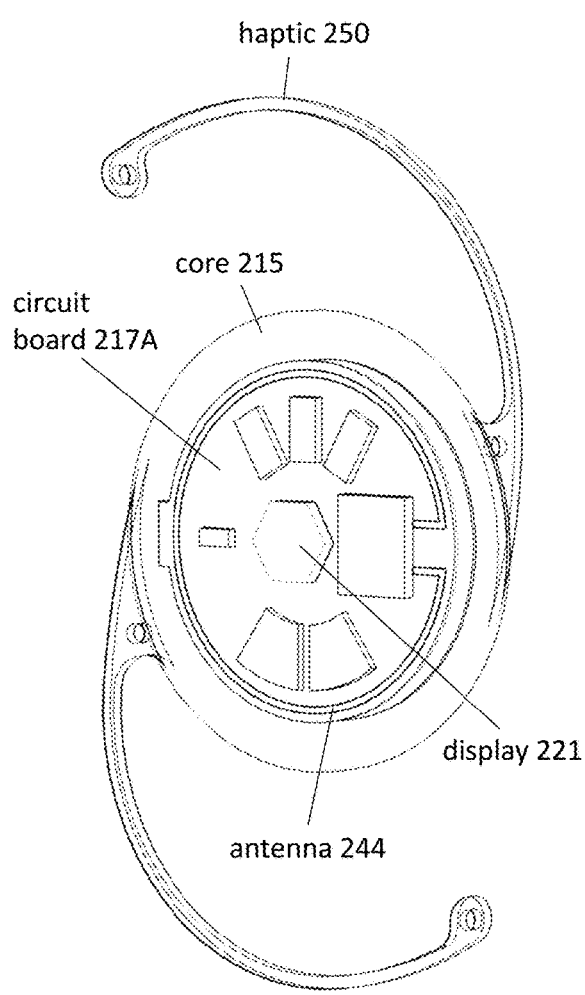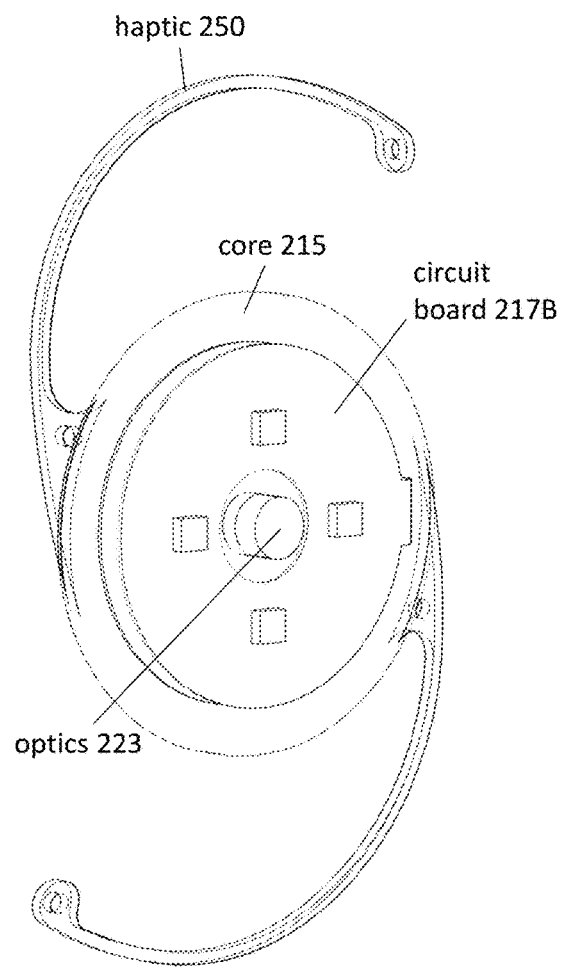
Fig. 2A
Fig. 2B

COMPENSATING CORNEAL OPACITY

CROSS-REFERENCE TO RELATED APPLICATION(S)

This application is a continuation of International Application No. PCT/US21/23462, "Electronic Intraocular Devices," filed Mar. 22, 2021; which claims priority to (i) U.S. Provisional Patent Application Ser. No. 62/993,607, "Bypassing Corneal Opacity to Restore Sight," filed Mar. 23, 2020, (ii) U.S. Provisional Patent Application Ser. No. 63/064,354, "Intraocular Femtoprojector," filed Aug. 11, 2020, and (iii) U.S. Provisional Patent Application Ser. No. 63/149,962, "Electronic Capsular Tension Ring," filed Feb. 16, 2021. The subject matter of all of the foregoing is incorporated herein by reference in their entirety.

BACKGROUND

1. Technical Field

This disclosure relates generally to electronic intraocular devices.

2. Description of Related Art

In an example of accidents that are rare but catastrophic, a dairy farm worker was cleaning the walls of a farm building with a corrosive disinfectant containing potassium hydroxide, a caustic, strong base. The pump sprayer he was using ruptured and sprayed disinfectant in his face, leaving him permanently blind in both eyes. Other well-known causes of accidental blindness include battery acid burns suffered as a result of incorrect automobile jump starting technique and burns from playing with fireworks.

The cornea is the clear tissue that in normal eyes lets light into the eyeball. The cornea-air interface provides most of the focusing power of the eye with some additional focusing occurring in the crystalline lens behind the iris. Focused light forms images on the retina.

Diseases, burns and injuries to the cornea cause blindness if the cornea becomes opaque. A cornea transplant can restore sight, but transplants depend on the availability of donor corneas and are not recommended in cases where the cornea has become vascularized as is often the case with chemical burns. About 13 million people worldwide are waiting for cornea transplants.

BRIEF DESCRIPTION OF THE DRAWINGS

Embodiments of the disclosure have other advantages and features which will be more readily apparent from the following detailed description and the appended claims, when taken in conjunction with the examples in the accompanying drawings, in which:

FIGS. 2A and 2B are perspective views of an electronic intraocular device with an open haptic.

DETAILED DESCRIPTION OF THE PREFERRED EMBODIMENTS

Figure 1A:
FIG. 1A shows a user with an implanted electronic intraocular device containing a femtoprojector.

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

An electronic intraocular device is implantable into the capsular bag of a wearer's eye. It may also be implanted in the wearer's eye, but anteriorly or posteriorly to the capsular bag. In some applications, the intraocular device includes a small projector, referred to as a femtoprojector. The femtoprojector projects images onto the wearer's retina when the electronic intraocular device is implanted in the wearer's eye. Different haptic designs may be used to keep the femtoprojector in position.

The electronic intraocular device may receive power and data wirelessly. The intraocular device may include a coil, for example around the periphery of a central core or around the periphery of the haptic if it is a closed form haptic. Power may be inductively transferred to this coil, and electronics may be used to condition and regulate this received power in order to power electronic components in the intraocular device. The electronic intraocular device may also contain an onboard battery and/or capacitor, which may be used to power electronic components in the device. The battery or capacitor may condition wirelessly received power and may also provide power during periods when wireless power is not available.

Electronic components in the data path may include a receiver, a data pipeline (e.g., decoding, image processing, timing), a display backplane (e.g., LED drivers), and a display frontplane (e.g., LED array). The frontplane generates an image, which is focused by projection optics onto the wearer's retina. In injuries in which the cornea has been damaged but the retina is still functioning, the intact retina senses these images, thus providing some vision capabilities to the wearer.

In some applications, the projected images may create the visual sensation of objects not present in the real world. For example, text may be projected onto the retina to allow the wearer to read a book even though there is no physical book present. Drawings, photographs and video may also be projected. The projected images may also be images of real world objects. A camera captures images of the real world, and these images or processed versions of these images are projected by the femtoprojector onto the wearer's retina. In this way, the wearer can "see" the real world. If the camera is looking where the wearer is facing and if the image capture and projection occurs in real time, then a sort of replacement vision is provided.

If the camera is mounted in eyeglasses or other headgear, but not on the wearer's eye, then the camera's view will follow the wearer's head motion but not their eye motion. Alternatively, if eye tracking is also implemented, then the images sent to the intraocular projector may be compensated for eye motion. Eye tracking components may be included in the electronic intraocular device. If eye tracking components are contained in both the electronic intraocular device (moving with the eye) and on the head (moving with the head, but not the eye), the pointing direction of the eye relative to the head may be used to determine which portion of the imagery captured by a head-mounted camera should be used as the replacement vision.

In another approach, the imager is mounted on the wearer's eye, such as in a contact lens worn by the wearer. In that case, the imager will move with the wearer's eye and the image capture will automatically account for both head and eye motion. If the imager and femtoprojector are aligned, then images captured by the contact lens imager may be relayed to the intraocular femtoprojector. This may be done wirelessly, for example by inductively coupled coils, radio transmission using antennae, ultrasonic transmission, capacitive coupling, through-body transmission or optical or infrared transmission.

Such a system that includes an intraocular video femtoprojector coupled to a contact lens containing an imager may be used to restore sight to patients with corneal opacity. Ordinary eyeball appearance may also be provided if the contact lens is colored appropriately. The imager mounted in the contact lens is naturally aimed to wherever the person's eye is "looking"—it is self-aligning. Further, in some cases the contact lens need not pass light, so the contact lens may be partially or even completely opaque. An electronic payload may occupy the center of the lens, in what would otherwise be the optical zone of a lens that transmits light. Additionally, in some cases the contact lens need not include a mechanism to oxygenate the cornea. One factor that contraindicates a cornea transplant is vascularization of the cornea following a burn, trauma or certain diseases. However, vascularization is beneficial for oxygenation. Blood vessels transport oxygen to tissues. This means that a vascularized cornea may not need a contact lens to transmit as much, or even any, oxygen as is required for conventional contact lenses.

The use of intraocular projectors is not limited to wearers with damaged corneas. In cataract surgery, the crystalline lens is replaced by an artificial lens. It may instead be replaced by an electronic intraocular device which contains an artificial lens at its center but also contains femtoprojector(s) or other electronics outside the center. In cases where the cornea is in good condition, the intraocular device may contain a variable focus lens, for example to provide improved eye accommodation.

Figure 1B:
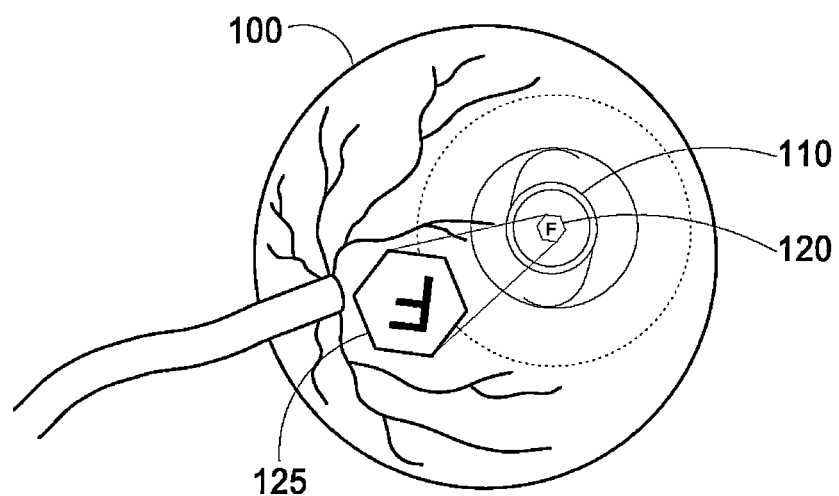
FIGS. 1B and 1C are a perspective view and a cross-sectional view of the electronic intraocular device implanted in the capsular bag of the user's eye.
Figure 1C:
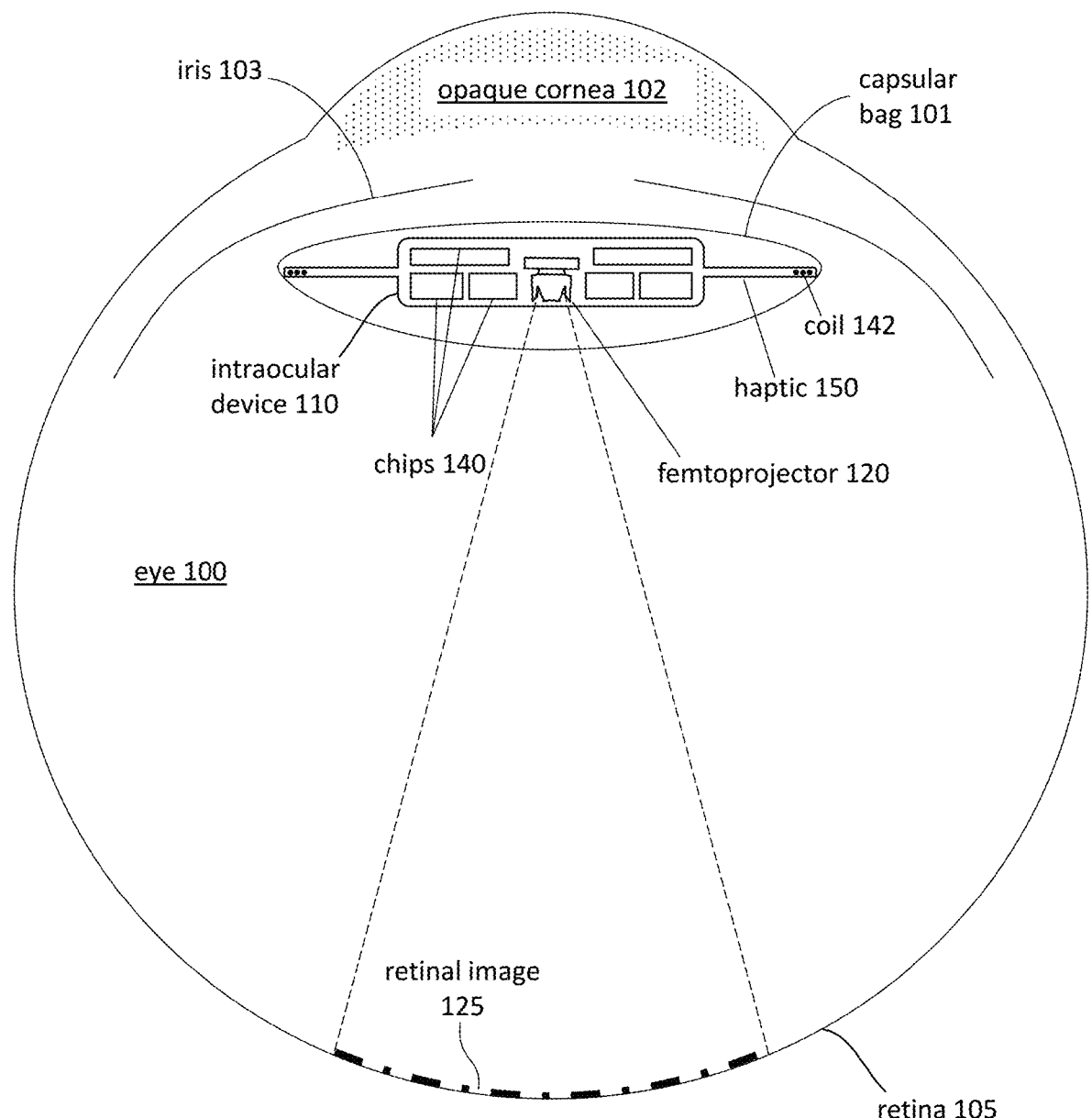

In more detail, FIG. 1A shows a patient with corneal opacity, where implanted electronic intraocular devices 110 restore some sight. FIGS. 1B and 1C are a perspective view and a cross-sectional view of the electronic intraocular device 110 implanted in the capsular bag 101 of the patient's eye 100. For completeness, FIG. 1C shows some of the structure of the eye 100, including the capsular bag 101, cornea 102, iris 103, and retina 105. The patient's cornea 102 is damaged and opaque in this example. The capsular bag 101 normally contains the crystalline lens of the eye, but the lens has been removed and replaced by the intraocular device 110 using surgical techniques.

As shown in FIGS. 1B and 1C, the electronic intraocular device 110 contains a femtoprojector 120. The femtoprojector 120 is a small projector that projects images inward onto the user's retina. In this example, it is located in a central region of the intraocular device 110, but it may also be located off center in other designs. The femtoprojector 120 typically includes an electronics backplane (e.g., driver circuitry), a frontplane of light emitting elements (e.g., an LED array), and projection optics. The frontplane produces an image (referred to as the source image), which is optically projected by the projection optics through the various eye structures and onto the retina 105, as shown in FIG. 1C. The image 125 on the retina causes a visual impression of sight. The femtoprojector 120 typically is not larger than 2 mm×2 mm×2 mm.

The electronic intraocular device 110 also includes other electronics 140, which are shown as rectangles in FIG. 1C. Electronic components 140 in the intraocular device may include microprocessors/controllers, motion sensors (such as accelerometers, gyroscopes and magnetometers), radio transceivers, power circuitry, antennas, batteries, elements for receiving electrical power wirelessly (e.g., coil 142), and fuses or other safety components to disable the intraocular device. Other components in the device may include passive components such as resistors, capacitors, and inductors; flex board or rigid printed circuit boards (PCB); optical and electro-optic components such as LEDs, image sensors and optics such as mirror and lenses; and other sensors such as pressure or biomarker sensors. For clarity, connections between the femtoprojector, electronics and coil are not shown. Because the cornea 102 is opaque, the femtoprojector 120 and electronics 140 may be positioned in a central region of the intraocular device 110, whereas this positioning would obstruct the vision of a person with normal eyesight. This provides more space for components in the intraocular device.

FIG. 1C shows a cross sectional view of the electronic intraocular device implanted in the user's eye. The portion of the intraocular device 110 containing the electronics preferably has a thickness that is less than 2 mm, an area of less than 30 mm², and a weight of less than 0.1 g. The femtoprojector 120 projects an image onto the user's retina. This is the retinal image 125 shown in FIG. 1C. In FIG. 1C, the cornea 102 is opaque so no light is imaged from the external environment. The retinal image 125 is projected against an otherwise dark background. The intraocular device may be opaque in order to provide a dark background even if there is some light leakage through the cornea 102. A haptic 150 keeps the femtoprojector 120 in position within the capsular bag 101, so that the retinal image 125 is stabilized and projected to the correct location on the retina.

In addition to the intraocular devices 110, the system may use other components to provide functionality. Some portions of the system may be entirely external to the user, while other portions may be worn by the user in the form of a headpiece or glasses. Components may also be worn on a belt, armband, wrist piece, necklace, or other types of objects. In other examples, the components may be in devices or structures near the user (e.g., the wall of a room, a tabletop data transmission system, etc.). Data and power may be transmitted to and from the intraocular devices 110 via wireless channels. Some embodiments discussed below show examples where some components are contained in a contact lens also worn by the user.

FIGS. 2A and 2B are perspective views of an electronic intraocular device with an open haptic 250. FIG. 2A is an anterior view (i.e., view of the front side facing outwards towards the external environment) and FIG. 2B is a posterior view (i.e., view of the back side facing inwards towards the retina). The intraocular device has a core 215 that contains the electronics, including the femtoprojector. The flexible haptic 250 extends away from the core 215 and keeps the core in a stable position within the capsular bag. In this example, the core 215 contains two circular circuit boards 217A and 217B, which contain various electronic components represented by the different shapes. The circuit boards 217 contain conductors to connect the different components, both within each circuit board and also between the two circuit boards. The femtoprojector is mounted on the front circuit board 217A and projects through a hole in the rear circuit board 217B. Electronics 221 for the femtoprojector is visible in FIG. 2A, and the projection optics 223 is visible in FIG. 2B. Antenna 244 is also shown in FIG. 2A. A coil for inductive power charging may also be incorporated onto the circuit boards 217.

In FIG. 2, the femtoprojector 120 and electronics are sealed to protect them from the eye environment and vice versa. For example, the components may be encapsulated in plastic such as poly(methyl methacrylate) (PMMA). Electronics boards may additionally have moisture resistant thin coatings applied, such as Paralyene or other materials, before being encapsulated by a low moisture content material like PMMA. In one design, the encapsulation (core 215) is rigid throughout, while the haptic 250 is flexible. In an alternative design, the circuit boards 217 and encapsulation may be flexible so that the central core may also be flexible, allowing the intraocular device to be bent into a smaller size for insertion into the patient's eye. For example, see FIG. 8B below. The outer surface of the intraocular device 210 may be curved to form a refractive interface that serves as a lens or performs some other optical function.

Figure 3:
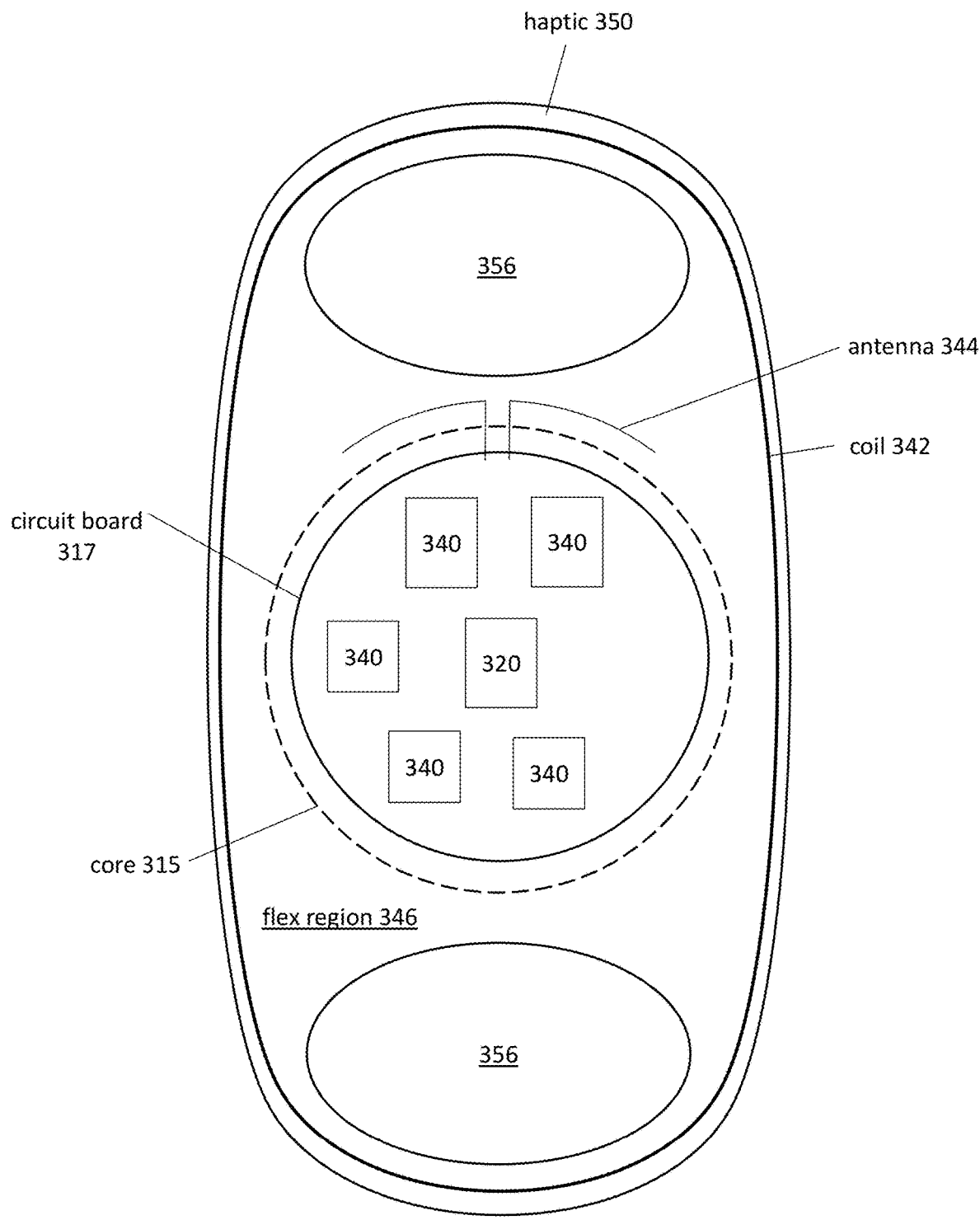
FIG. 3 is a plan view of an electronic intraocular device with a closed form haptic.

FIG. 3 is a plan view of an electronic intraocular device with a closed form haptic. The perimeter of the intraocular device, including haptic, is a convex shape. In this design, the central core 315 containing the circuit board 317, femtoprojector 320 and other integrated circuits 340 is rigid or semi-rigid. The area 346 outside the central core is flexible.

This flexible region includes an antenna 344 for data transfer and a coil 342 for power transfer. Alternatively, data may be modulated onto the power signal so that no additional antenna is required. The antenna may be a 5 GHz λ/2 dipole antenna or other radio frequency antenna. The antenna 344 and coil 342 are encapsulated in a flexible material such as silicone. Region 346 also functions as a haptic 350 to keep the femtoprojector in position within the capsular bag. Cutouts 356 increase the flexibility of the haptic and reduce the overall weight. Because the haptic 350 is a closed form, a coil 342 may be implemented around the perimeter of the entire flex region 346. This increases the area enclosed by the coil 342 compared to a coil that encircles only the central core 315, which in turn improves inductive power transfer since inductive power transfer is proportional to the square of the enclosed area. In FIG. 3, the plan view of the intraocular device is drawn as an oblong shape with rounded corners. However, it may take any shape, including oval, circular, rectangular or other polygonal shape. The intraocular device of FIG. 3 may fit within lateral dimensions of about 8 mm by 11 mm, and a thickness of about 5 mm.

Figure 4:
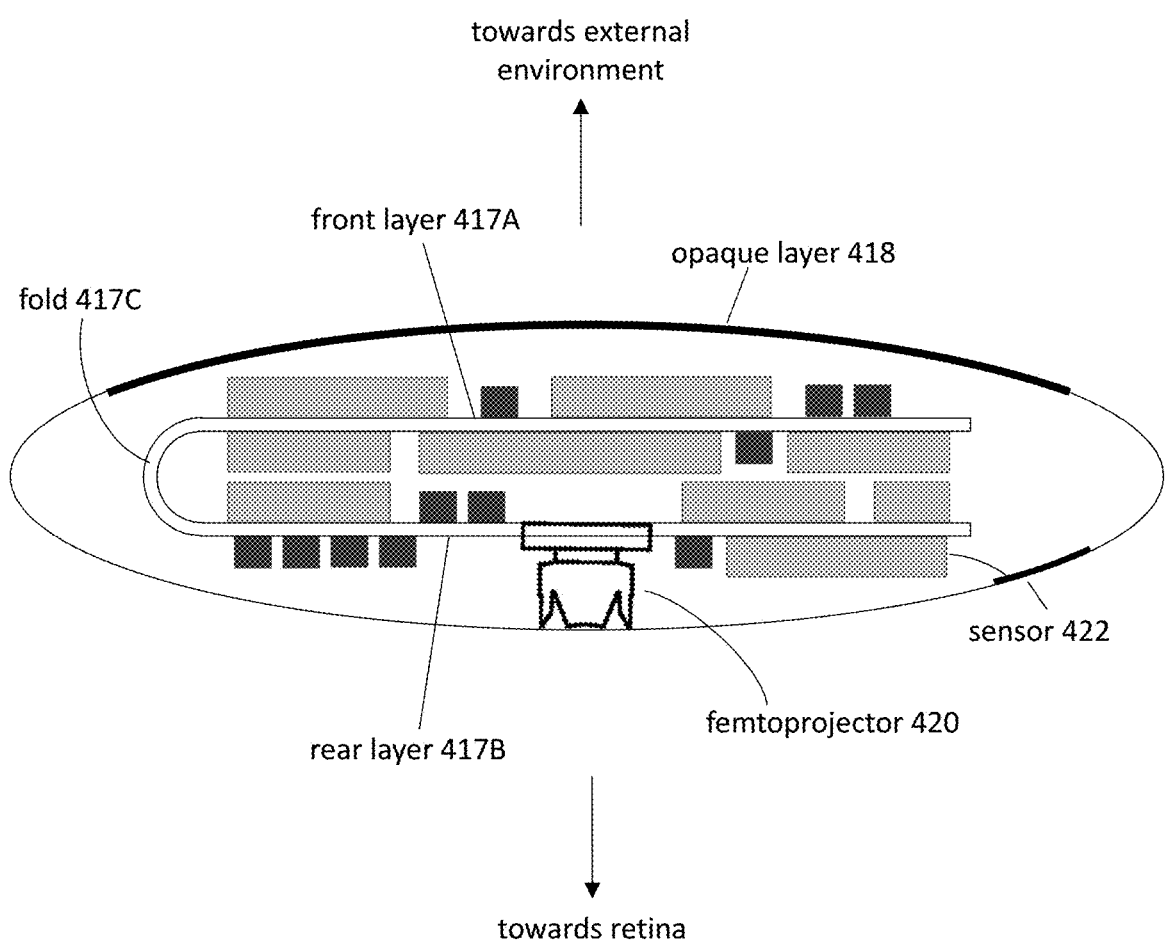
FIG. 4 is a cross-sectional view of an electronics assembly using a flexible circuit board folded into two layers.
Figure 5:
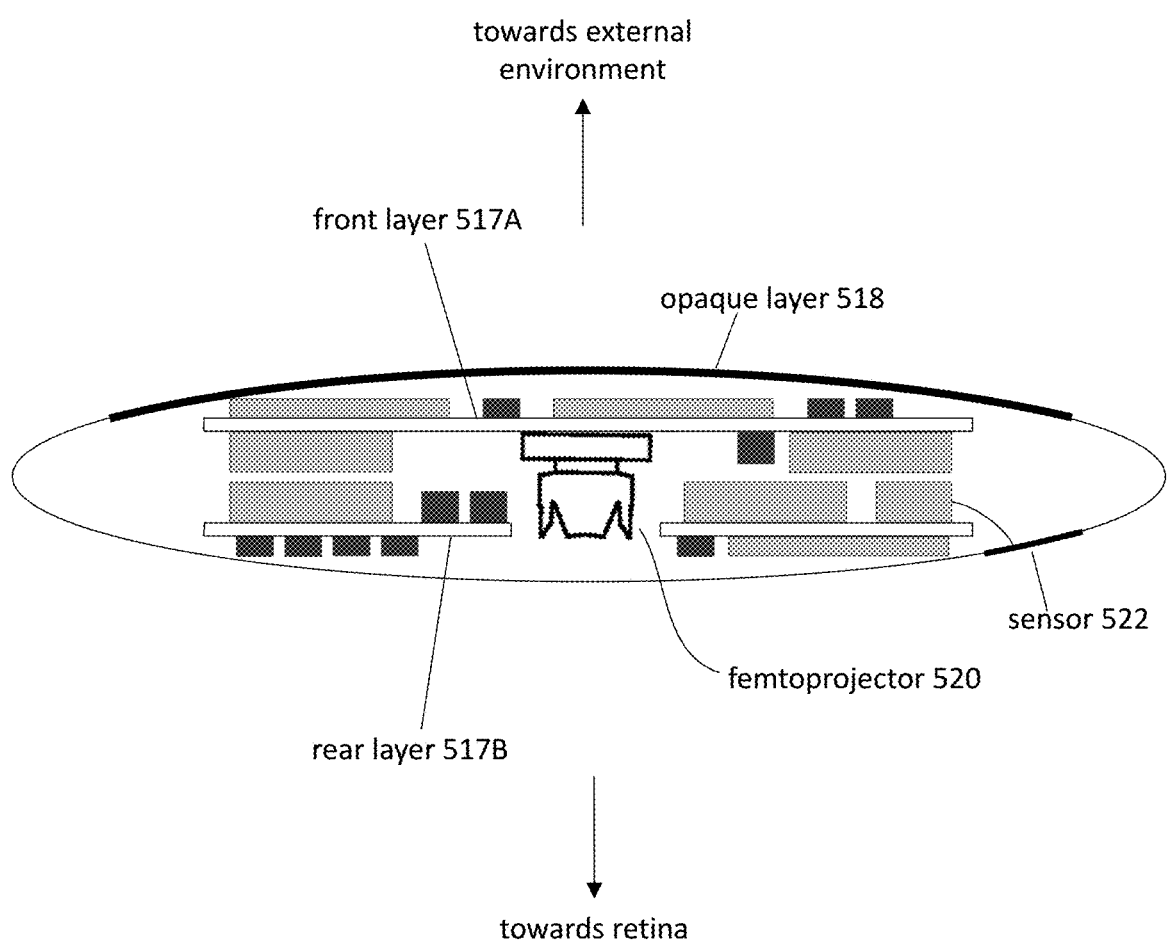
FIG. 5 is a cross-sectional view of an electronics assembly using a multi-layer circuit board.

FIGS. 4 and 5 are cross-sectional views of electronics assemblies using multiple layers of circuit boards. In alternative embodiments, electronic components could be wire bonded and suspended in a molding process. FIGS. 4 and 5 show only the portion of the intraocular device containing the circuit boards. The haptic is not shown. In FIG. 4, a single flexible circuit board is folded at 417C to form the two layers 417A and 417B. The components, shown as rectangles in FIG. 4, may be mounted to the single circuit board before it is folded and then the circuit board is folded to form the two layers. Electrical connections between the two layers 417A,B may be implemented on the circuit board across the fold 417C, so that no external connections between the folded layers 417A,B are required. In this example, the femtoprojector 420 is mounted to the rear layer 417B, facing the retina. The core also includes an opaque layer 418 which blocks light from the external environment, thus creating a darker background for the images from the femtoprojector. The opaque layer 418 may be an absorbing material such as carbon, roughened or etched nickel ("nickel black"), black chrome, Vantablack (Surrey NanoSystems, Newhaven, UK), or black indium-tin oxide.

The design shown in FIG. 4 also includes an additional sensor 422. This may be a pressure sensor, which measures the internal eye pressure. Depending on the type of sensor, it may or may not be exposed to the eye environment.

In FIG. 5, the two layers 517A and 517B are two separate "stacked" circuit boards. Electrical connections between the two layers 517 may be implemented by wire bonds, ribbon cable, or a flex board connected to a rigid board with a multipin connector. The femtoprojector 520 is mounted on the front layer 517A and protrudes through a hole in the rear layer 517B. This may reduce the overall thickness of the electronics assembly.

In alternate embodiments, more than two boards may be stacked. They may be stacked to different depths in different regions of the device. These boards may also have holes, cutouts or other affordances for components mounted on other boards. Components on different boards may be electrically connected by connectors, board-level vias or folds, for example.

Figure 6:
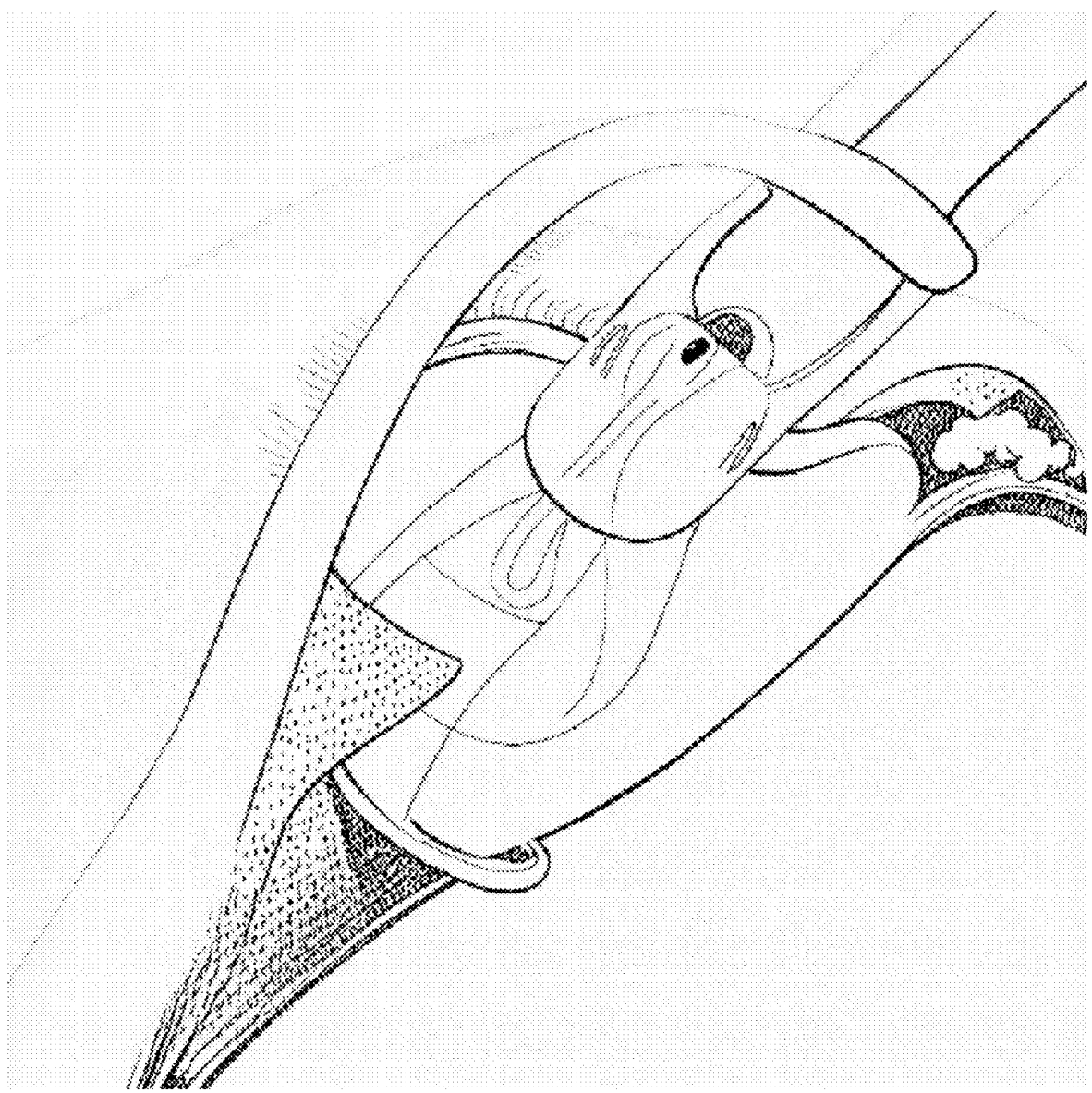
FIG. 6 shows folding the electronic intraocular device for insertion into the capsular bag.

FIG. 6 shows folding the electronic intraocular device for insertion into the capsular bag. The areas of the intraocular device outside the core electronics, such as the haptic, may be made flexible to facilitate folding of the device. The core electronics may also have some degree of flexibility, depending on the design. An incision is made in the cornea to gain access to the capsular bag. The crystalline lens is removed from the capsular bag. The electronic intraocular device is folded to reduce its size and then inserted into the capsular bag through the incision. The intraocular device unfolds inside the capsular bag to its correct shape and size. The haptic positions the intraocular device within the patient's eye. In an alternative approach, the entire cornea may be temporarily removed, the intraocular device inserted into the capsular bag, and then the cornea replaced. Other surgical techniques may also be used.

Figure 7A:
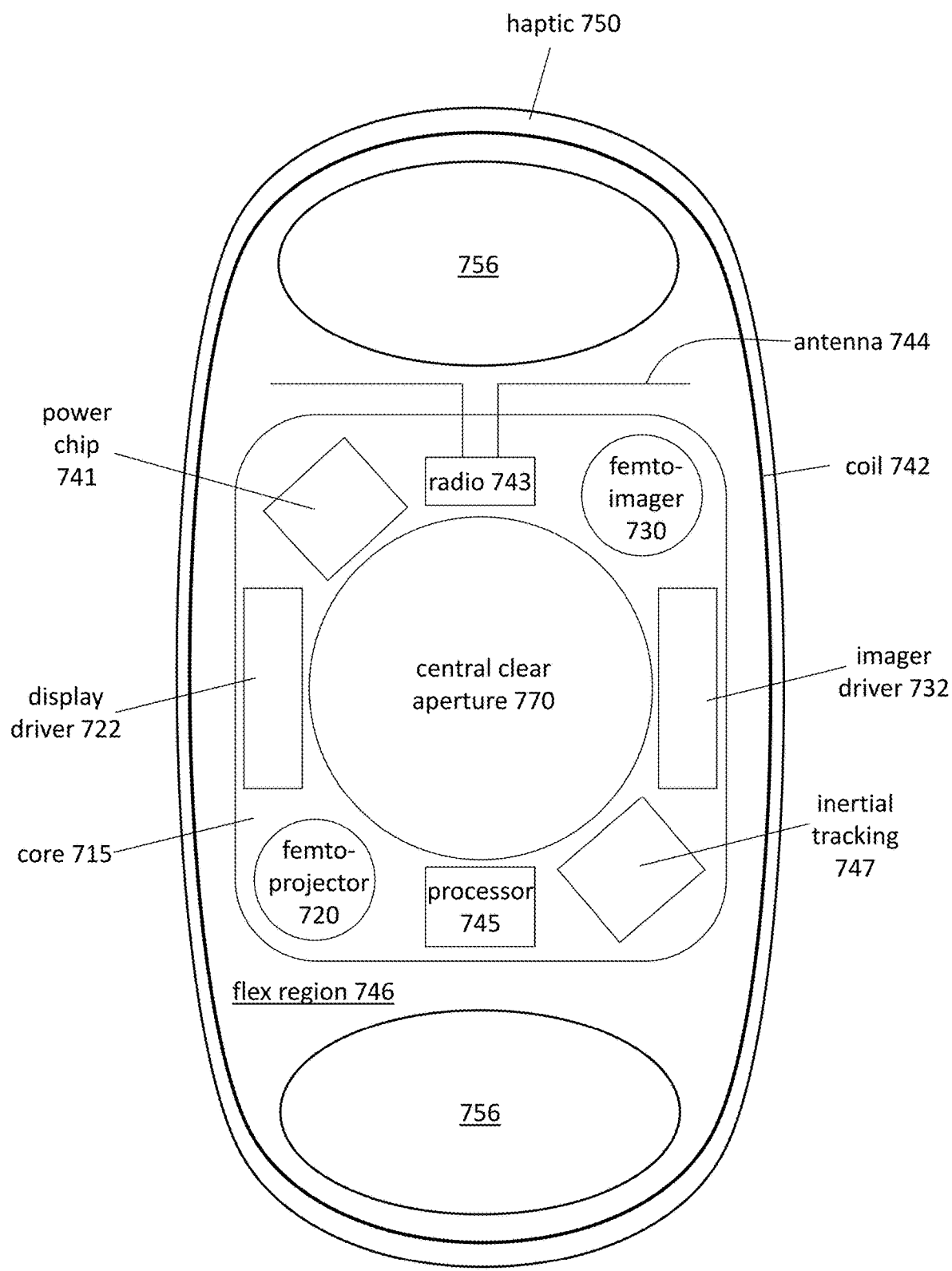
FIGS. 7A and 7B are a plan view and cross-sectional view of an electronic intraocular device with a clear central aperture.
Figure 7B:
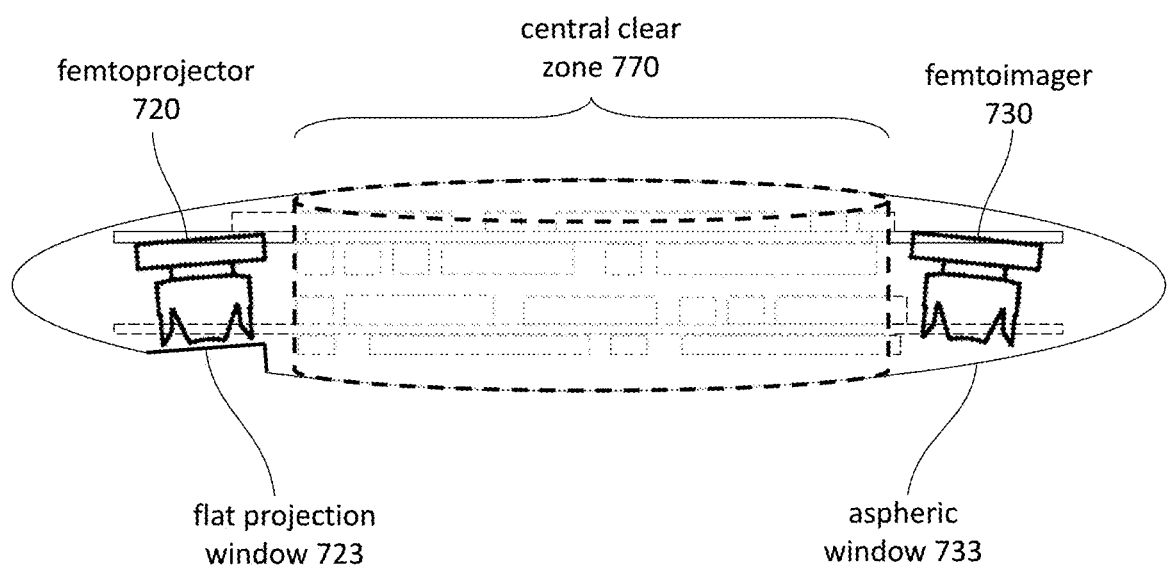

FIGS. 7A and 7B are a plan view and cross-sectional view of an electronic intraocular device with a clear central aperture. This device uses the same closed form haptic design 750 with cutouts 756 as FIG. 3, but it has a central clear area 770. For example, the user may have a clear cornea and some regular vision. A replacement lens may be incorporated into this clear region 770. The electronics core 715, which may be rigid, semi-rigid or flexible, has a donut shape with a hole in the middle. In this example, the electronic intraocular device includes a small imager (femtoimager 730) in addition to the femtoprojector 720. The femtoimager 730 may be used to capture images of the patient's fundus, or may be facing outward to collect images of what the user sees in the surrounding environment. Optical rays from the femtoprojector 720 to the retina and from the retina to the femtoimager 730 (if the femtoimager is facing inwards) cross the interface between the intraocular device and the interior of the patient's eye. This interface may be shaped to improve the projection or imaging of these devices. In FIG. 7B, the femtoprojector projects light through a flat interface 723, while the femtoimager receives light through a curved (possibly aspheric) surface 733. The electronics labeled in FIG. 7A include power chip 741, radio 743, display driver 722 for the femtoprojector, imaging driver 732 for the femtoimager 730, a processor/controller 745 and inertial tracking components 747 such as accelerometers, gyroscopes and magnetometers. Alternatively, some of the electronics components (e.g., the femtoprojector 720) may be located in the central clear aperture 770, but occupying a small enough area that most of the aperture is not occluded.

Figure 8A:
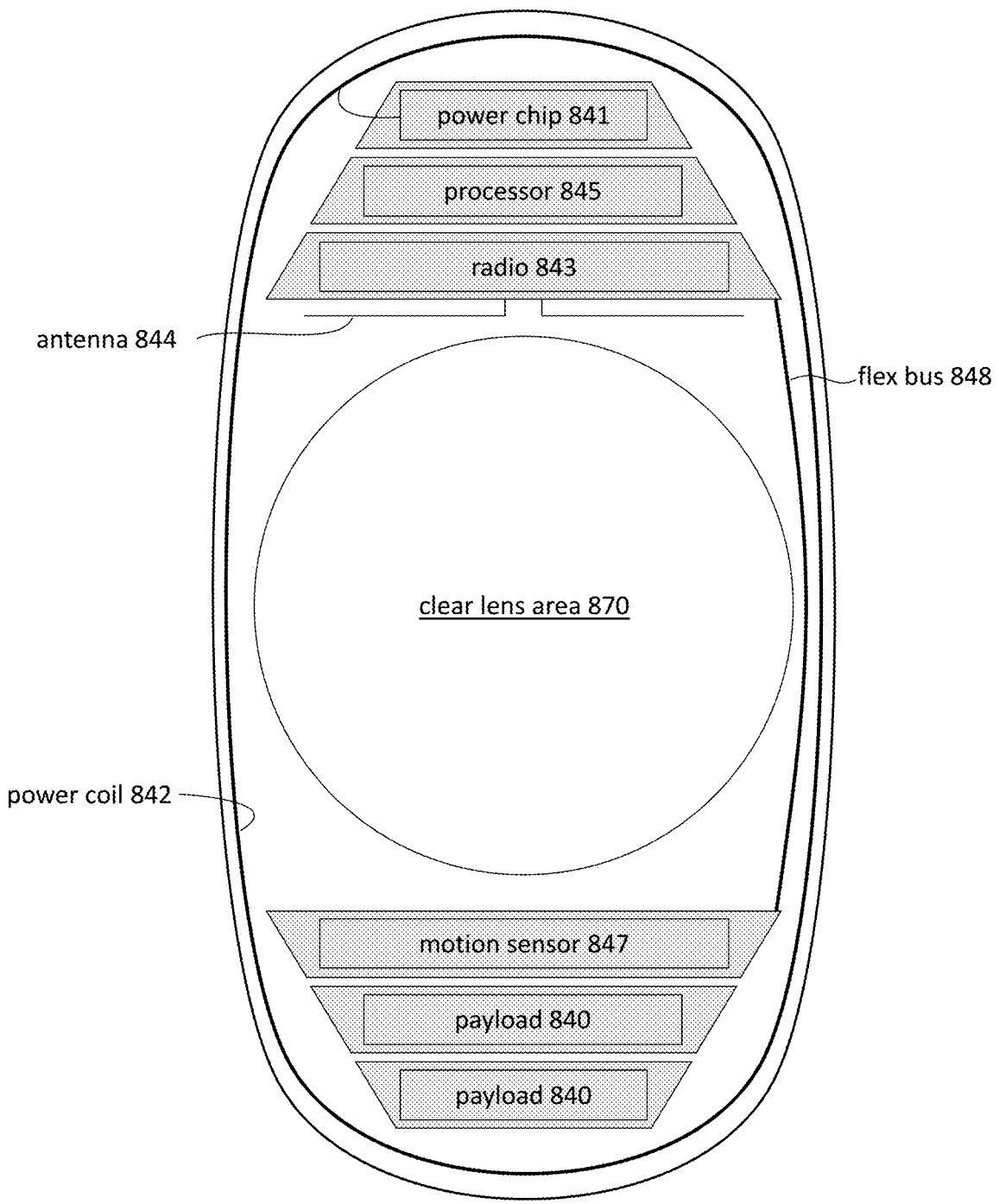
FIG. 8A is a plan view of another electronic intraocular device without a femtoprojector.

FIG. 8A is a plan view of another electronic intraocular device without a femtoprojector or femtoimager. A power chip 841, processor 845, radio 843 with antenna 844, and motion sensor 847 are shown, but other or different payloads 840 may also be used. This intraocular device has a central clear area 870, where a replacement lens 872 (shown in FIG. 8B) may be incorporated. However, the electronics are moved to the sides compared to the design of FIG. 7A. This allows the central clear aperture 870 to be made larger. In addition, each electronics component is wide in one direction and narrow in the other direction, and they are not all mounted on a common rigid circuit board. Rather, each component is mounted on a section of circuit board but the regions between components are flexible to facilitate bending of the intraocular device along creases between the components. In one approach, multiple components (e.g., power chip 841, processor 845 and radio 843) are mounted on a common flexible circuit board, but the circuit board is flexible between the components. In a different approach, each component is mounted on its own circuit board, and connections between the components are made using flexible connectors (e.g., flexible bus 848 in FIG. 8A).

Figure 8B:
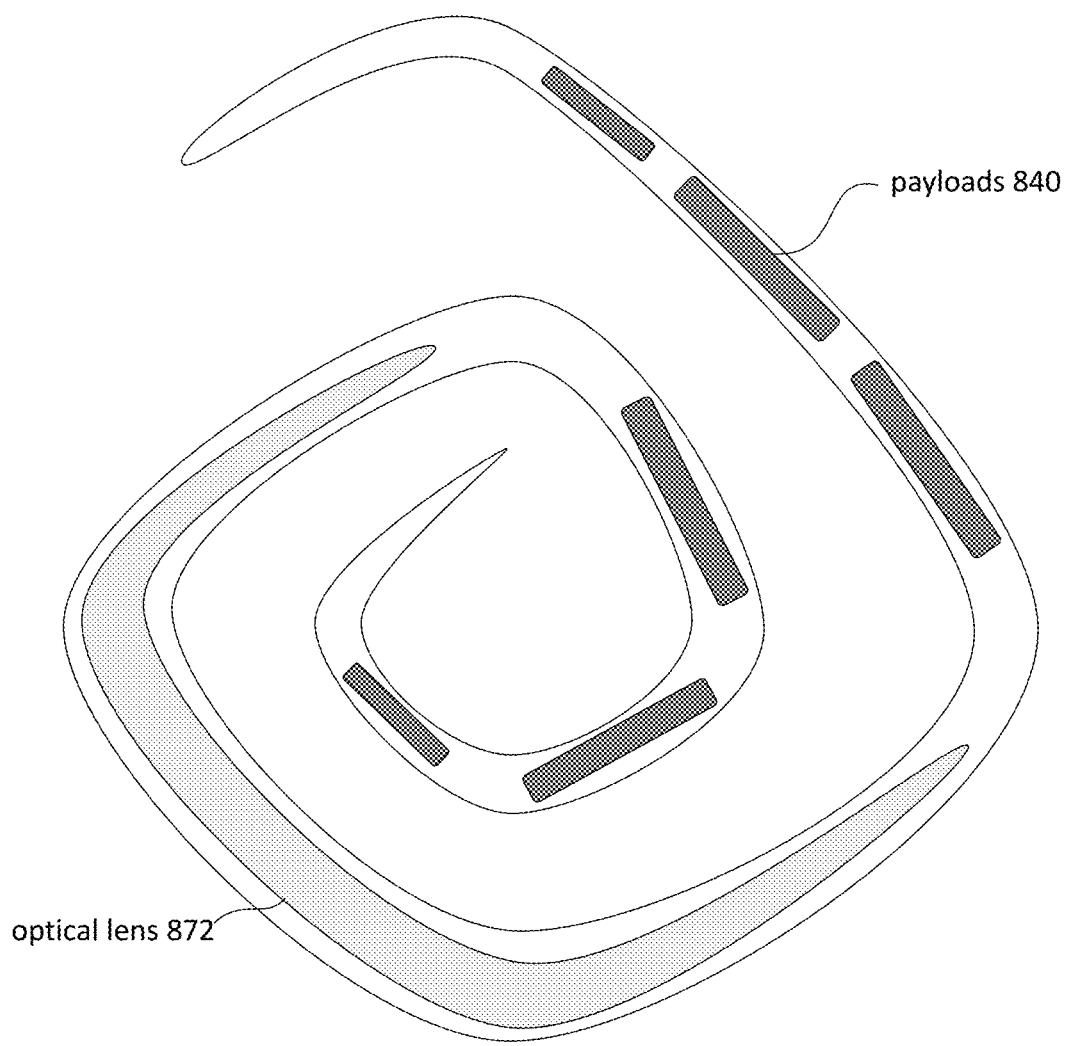
FIG. 8B shows folding the electronic intraocular device for insertion into the capsular bag.

FIG. 8B shows folding the electronic intraocular device for insertion into the capsular bag. The electronic components 840 remain flat, but the intraocular device is bent between components.

Figure 9:
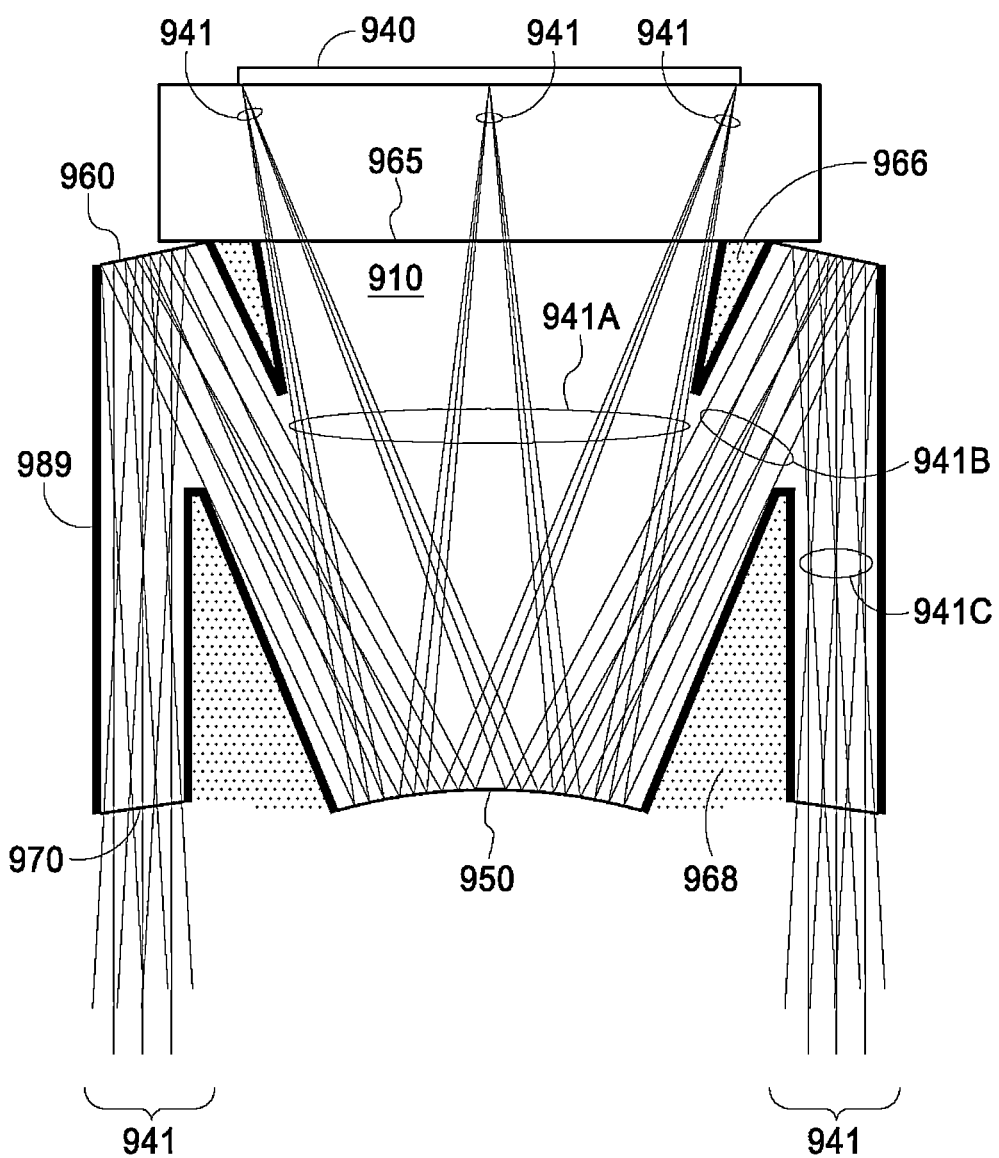
FIG. 9 is a cross-sectional view of a femtoprojector suitable for use in an electronic intraocular device.

FIG. 9 is a cross-sectional view of a femtoprojector suitable for use in an electronic intraocular device. The femtoprojector includes an image source 940 and an optical projection system. FIG. 9 is drawn to scale and the projection optics is approximately 1.0 mm in diameter. A solid transparent substrate 910 forms the core of the projection optics. The projection optics includes a concave primary mirror 960 and a convex secondary mirror 950. Either or both of these may be aspheric. The concave primary mirror 960 may be formed by coating a surface of the substrate 910 with a reflective material such as a metal (e.g. aluminum or silver) or an engineered stack of dielectric layers. The shape of the primary mirror 960 may be made by any of several different techniques. For example, if the substrate 910 is injection-molded plastic, then the shape of the primary mirror 960 follows the shape of the mold used. Alternatively, the shape of the primary mirror 960 may be made by diamond turning the substrate on a lathe. Alternatively, the shape of the primary mirror 960 may be made by photolithography and etching steps. Gray scale photolithography may be used to etch a mirror surface profile, for example. Wafer scale optics techniques including embossing, compression molding and/or UV curing photosensitive polymers may also be used to form mirror profiles. Additive manufacturing or three-dimensional printing (e.g. via two-photon polymerization) techniques may also be employed.

The primary mirror 960 includes a clear input aperture 965. An image source 940, such as an LED (light emitting diode) display chip with an array of individually addressable emitters, is mounted at this location. In FIG. 9, the image source 940 is slightly separated from the input aperture 965. The spacing is shown as a rectangle in FIG. 9. It may be a glue layer to attach the image source 940 to the input aperture 965. Alternative image sources include illuminated photomasks or single light emitting diodes, as examples. Of course, video is more exciting than a static pattern or one with only very few pixels. However, these more limited image sources are useful for some applications.

The secondary mirror 950 faces the image source 940, and the primary mirror 960 faces the secondary mirror 950. The secondary mirror 950 may be formed using similar techniques as the primary mirror 960, for example by coating the substrate 910 with a reflective material. Light rays from the image source 940 are first incident on and reflected by the secondary mirror 950, which is convex in this example. The reflected rays are then incident on and further reflected by the primary mirror 960 before exiting the optical system through the annular output aperture 970. The primary mirror 960 is larger than the secondary mirror 950. The secondary mirror 950 may be larger or smaller than the opening 965 in the primary mirror.

The secondary mirror 950 and primary mirror 960 cooperate to project the image from the image source 940 out the output aperture 970 and onto the user's retina. However, not all light rays from the image source 940 are included in image formation. Those light rays that are projected to form an image are referred to as image-forming rays 941. The remaining light rays from the image source 940 are referred to as stray rays. In FIG. 9, the output aperture 970 is annular in shape, but not required to be planar. The output aperture 970 limits which rays propagate to the eye to form the image. In the design of FIG. 9, the output aperture 970 is approximately axially aligned with the convex secondary mirror 950, and the input aperture 965 is approximately axially aligned with the concave primary mirror 960. The output aperture 970 may form a refractive interface and it may be curved or otherwise shaped to improve the imaging performance.

FIG. 9 shows the ray paths for image-forming rays 941 from the image source 940 to the output aperture 970, for rays from the left edge, center and right edge of the image source. Image-forming rays from other locations on the image source to the output aperture 970 will fall within the boundaries defined by the rays shown in FIG. 9. The aggregate of all image-forming rays may be divided into three ray bundles: a first bundle 941A of image-forming rays propagating from the image source 940 to the secondary mirror 950, a second ray bundle 941B propagating from the secondary mirror 950 to the primary mirror 960, and a third ray bundle 941C propagating from the primary mirror 960 to the output aperture 970 and then on to the retina.

In FIG. 9, there are two spaces between these image-forming ray bundles. One space 966, which will be referred to as the input interspace, is located between the first and second ray bundles 941A and 941B. The other space 968, which will be referred to as the output interspace, is located between the second and third ray bundles 941B and 941C. In FIG. 9, the interspaces 966 and 968 are stippled because they are empty space. There need not be any material in either interspace 966, 968. For example, a groove may be cut into the substrate 910.

Baffles may be positioned in these two interspaces to control stray rays without interfering with image-forming rays. For convenience, these will be referred to as the input baffle and output baffle, respectively. In the example of FIG. 9, the input baffle is a groove in the solid substrate 910 with two absorbing surfaces, represented by thick lines in FIG. 9. One surface is adjacent to the first ray bundle 941A, and one surface is adjacent to the second ray bundle 941B. The output baffle is also a groove with two absorbing surfaces: one surface which is adjacent to the second ray bundle 941B, and one surface which is adjacent to the third ray bundle 941C. Other types and shapes of baffles may also be used. For example, the input baffle may be a flat absorbing ring. The projection optics design also includes a side baffle 989. The baffles may be an integral part of the projection optics or a surrounding structure in which the optical system is mounted. In one implementation, the baffles are made by depositing an absorbing material such as carbon, roughened or etched nickel ("nickel black"), black chrome, or Vantablack (Surrey NanoSystems, Newhaven, UK) on surfaces of the transparent substrate 910. Black indium-tin oxide may also be used. The side baffle 989 may be separate from the substrate 910. For example, it may be an absorbing material deposited on the sides of a hole into which the core is inserted.

In FIG. 9, the baffle system is designed to block all of the stray rays that would have a direct path from the image source 940 through the output aperture 970, so that no stray rays have a direct path from the image source 940 to the user's retina. In other embodiments, the baffle system may block less than all of the stray rays, so the baffles may be shorter. Additional examples of projection optics are described in U.S. patent application Ser. No. 15/570,707 "Femtoprojector Optical Systems", Ser. No. 15/982,989 "Peripheral Femtoprojector Optical Systems", and Ser. No. 15/985,511 "Advanced Femtoprojector Optical Systems", which are all incorporated by reference herein.

Figure 10:
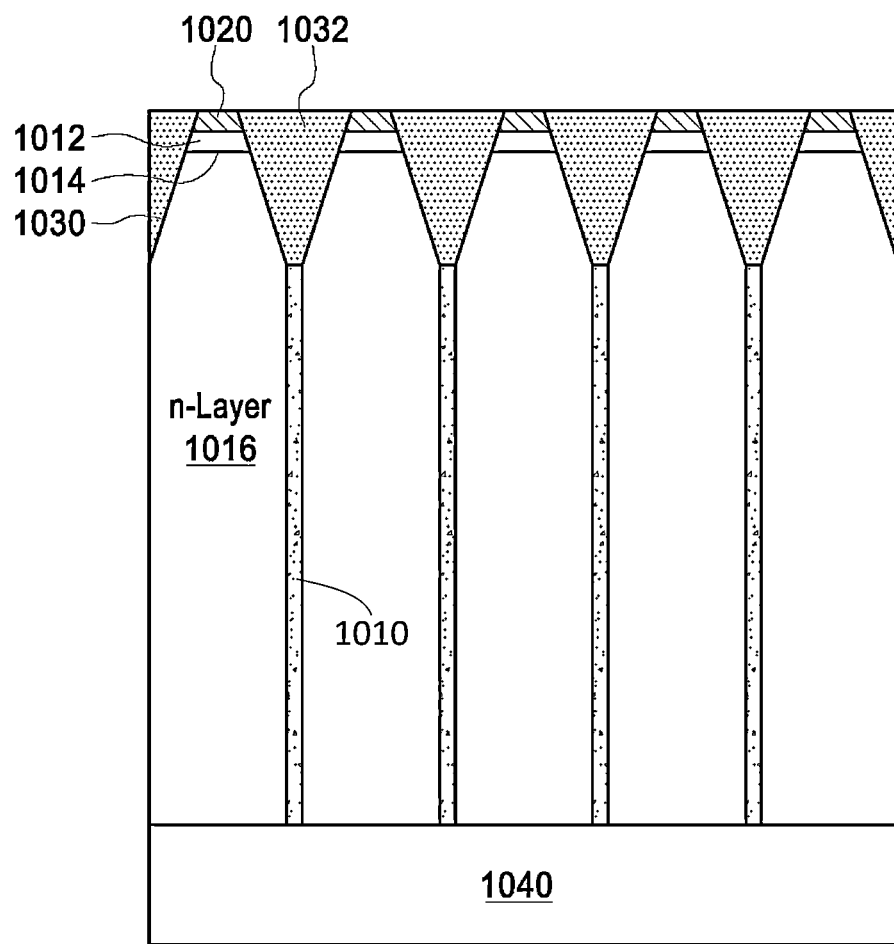
FIG. 10 is a cross-sectional view of an LED array suitable for use in an electronic intraocular device.

FIG. 10 is a cross-sectional view of an LED array suitable for use as the image source in an electronic intraocular device, such as image source 940 in FIG. 9. FIG. 10 is drawn to scale. The LED array in FIG. 10 uses a combination of a half cavity and sloped, straight reflective sidewalls to improve the power distribution so that more light falls within the collection angle of the projection optics. FIG. 10 is a cross-sectional diagram of an array of LEDs. Each LED includes a semiconductor stack with (from top to bottom in FIG. 1) p-layer 1012, active region 1014, and n-layer 1016. The active region 1014 may be a quantum well region. Other gain media include heterostructures and quantum dot layers. The LEDs also include a reflector 1020. The reflector 1020 and p-layer 1012 form a half cavity for light emitted from the active region 1014. The LED array also has angled reflective sidewalls 1030. The sidewalls are "straight," meaning that in cross-section they appear as lines. Their three-dimensional shape may be flat (e.g., a face of a pyramid) or conical. In this example, the sidewalls 1030 are constructed as a trench filled by a dielectric 1032. The sidewalls 1030 are reflective due to total internal reflection at the interface between the dielectric 1032 and the semiconductor stack. Here, they extend through the reflector 1020 and through the semiconductor stack into the n-layer 1016. The array also includes an encapsulation material 1040. In FIG. 10, light exits the image source through the encapsulation material 1040.

The half cavity formed by p-layer 1012 and reflector 1020, and the angled sidewalls 1030 together redistribute the light emitted from the active region so that more of it couples into the projection optics, which are not shown in FIG. 10. The set of rays collected by the projection optics will be referred to as the collection angle or collection cone of the projection optics, even though strictly speaking the set of rays may not span a cone. In one approach, the half cavity 1012/1020 concentrates the light from the active region into lobe(s), and the sidewalls 1030 reflect the lobe(s) to the direction normal to the semiconductor stack.

FIG. 10 is drawn to scale for a GaN (gallium nitride) LED array with pitch=1.3 um. The sidewalls 1030 have sidewall angle $\theta_{SW}$=15° as measured from vertical, and sidewall height $h_{SW}$=0.7 um tall. In this example, the p-layer 1012 is 0.17 um thick ($t_{HC}$=0.17 um), creating a half cavity that is 0.78 wavelengths. The n-layer 1016 is 5.5 um thick. Other designs will use other dimensions. For example, the pitch may be in a range of 0.5 μm to 2.0 um, with active regions having a width of 40% to 90% of the pitch. Such small pitches result in high aspect ratio structures. For example, the sidewalls may have heights in a range of 0.7 um to 1.5 um.

In FIG. 10, deep, vertical trenches 1010 are created between LED pixels and filled with absorptive metal such as chromium or tungsten. The reflectivity is high even for absorptive metals when the angle of incidence is higher (i.e., more oblique). For rays that are redirected by the half cavity and the sloped sidewalls to near normal, the reflection is high. Other rays experience higher absorption by the vertical absorptive metal and can be suppressed effectively after a few bounces.

In one approach, the half cavity creates an angular power distribution with one or more lobes, each of which produces maximum power along some angle from normal. For example, the first lobe may produce maximum power at an angle of 35° relative to normal and the second lobe may produce maximum power at an angle of 74°. The sidewalls may be tilted with a sidewall angle of 17.5°, which reflects the first lobe to the normal direction (0° angle). The sidewalls may be constructed so that the first lobe is reflected due to total internal reflection but the second lobe passes through the sidewall and is absorbed, thus reducing stray light.

Another aspect concerns the fabrication of such devices. The p-layer, quantum wells, and unintentionally doped n-layer may be about 0.7 um in total, and the total height of the LED stack may be significantly taller than 0.7 um if additional layers are added. On the other hand, LED arrays used in electronic intraocular devices may have pitches on the order of 2 μm or less, and individual structures within each pixel may be a fraction of the 2 um pitch. This results in individual structures with high aspect ratios, which are more challenging to fabricate.

In one fabrication approach, a semiconductor stack is epitaxially grown. From the substrate, the stack includes the thicker n-layer, the active region (e.g., quantum well), the thinner p-layer and the reflector layer. An array of trenches is etched through all the layers into the thicker n-layer. The trenches isolate the individual LEDs and the sides of the trenches form the sidewalls of the LEDs. The trenches are at least partially filled with a dielectric. This structure is planarized (e.g., using chemical mechanical polishing), creating a top surface comprising the reflector layer for each LED and the planarized dielectric between LEDs. Metal contacts to the reflector layer are formed on this flat top surface, for example by a liftoff process.

Additional examples of image sources are described in U.S. patent application Ser. No. 15/894,712 "Ultra-Dense LED Projector", Ser. No. 16/154,603 "Ultra-Dense LED Projector Using Thinned Gallium Nitride", and Ser. No. 16/692,767 "Ultra-Dense Array of LEDs with Half Cavities and Reflective Sidewalls", which are all incorporated by reference herein.

Figure 11A:
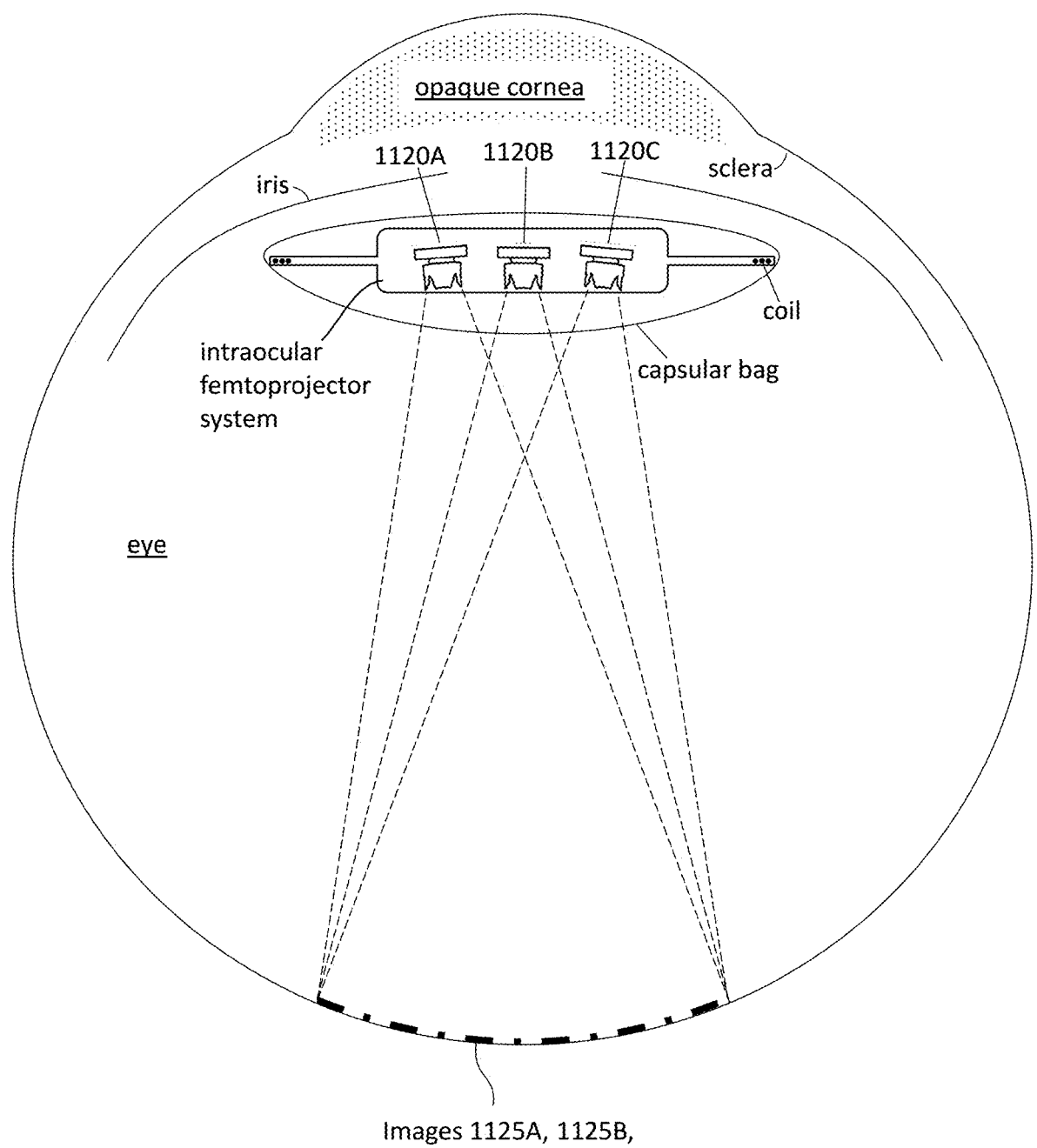
FIGS. 11A and 11B are cross-sectional views of electronic intraocular devices with multiple femtoprojectors.
Figure 11B:
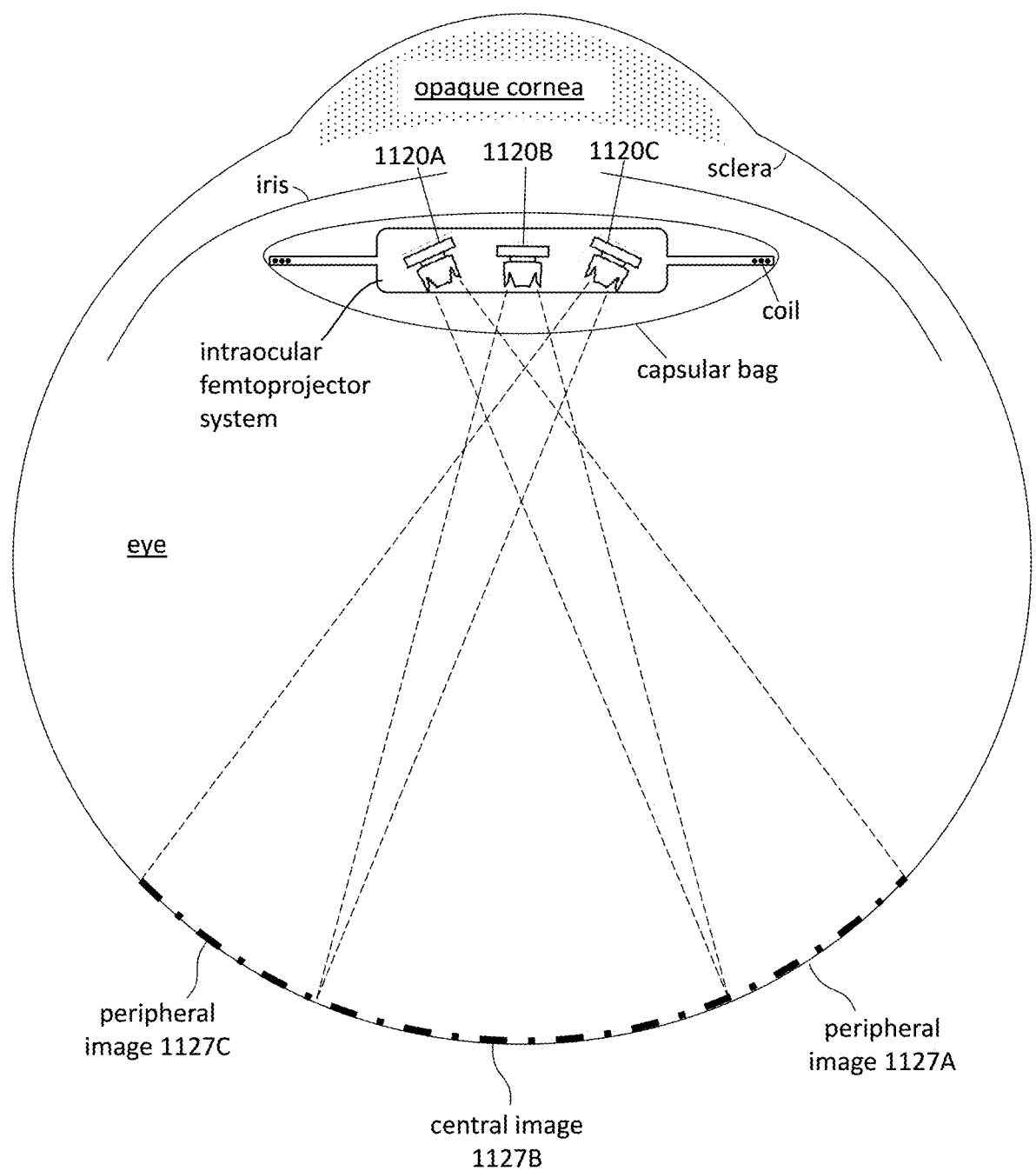

FIGS. 11A and 11B are cross-sectional views of electronic intraocular devices with multiple femtoprojectors. FIG. 11A shows three femtoprojectors 1120A,B,C that project images 1125A,B,C to the same location on the retina. For example, these femtoprojectors 1120A,B,C may be redundant. At any time, one of the femtoprojectors is operational and the other two are turned off. If one or two of the femtoprojectors is not functional, images may still be produced by the remaining femtoprojector(s).

Alternatively, the femtoprojectors may produce different components of the overall image, such as different color components. One femtoprojector 1120A produces a red image 1125A, one femtoprojector 1120B produces a green image 1125B, and one femtoprojector 1120C produces a blue image 1125C. The three images are overlaid at the retina to produce a color image for the user.

The femtoprojectors 1120 may also have different performance characteristics. They may differ in spatial resolution, brightness, dynamic range, frame rate and/or power consumption. Different femtoprojector(s) may then be selected and operated depending on the requirements of the application and/or of the images displayed. Furthermore, femtoprojectors may be aimed to project images away from scotomas or damaged areas of a retina. In some cases femtoprojectors may be aimed away from the fovea, e.g. if the fovea is damaged.

In FIG. 11B, the femtoprojectors 1120A,B,C project images 1127A,B,C to different sections of the retina. This may be used to stitch together images from the different femtoprojectors to create a larger aggregate image. Because the retina has the highest spatial resolution near the fovea and lower spatial resolution toward the periphery, the femtoprojectors may be designed with different resolutions. Femtoprojector 1120B which always projects to the fovea has the higher resolution, while the peripheral femtoprojectors 1120A,C have lower resolutions.

Figure 12A:
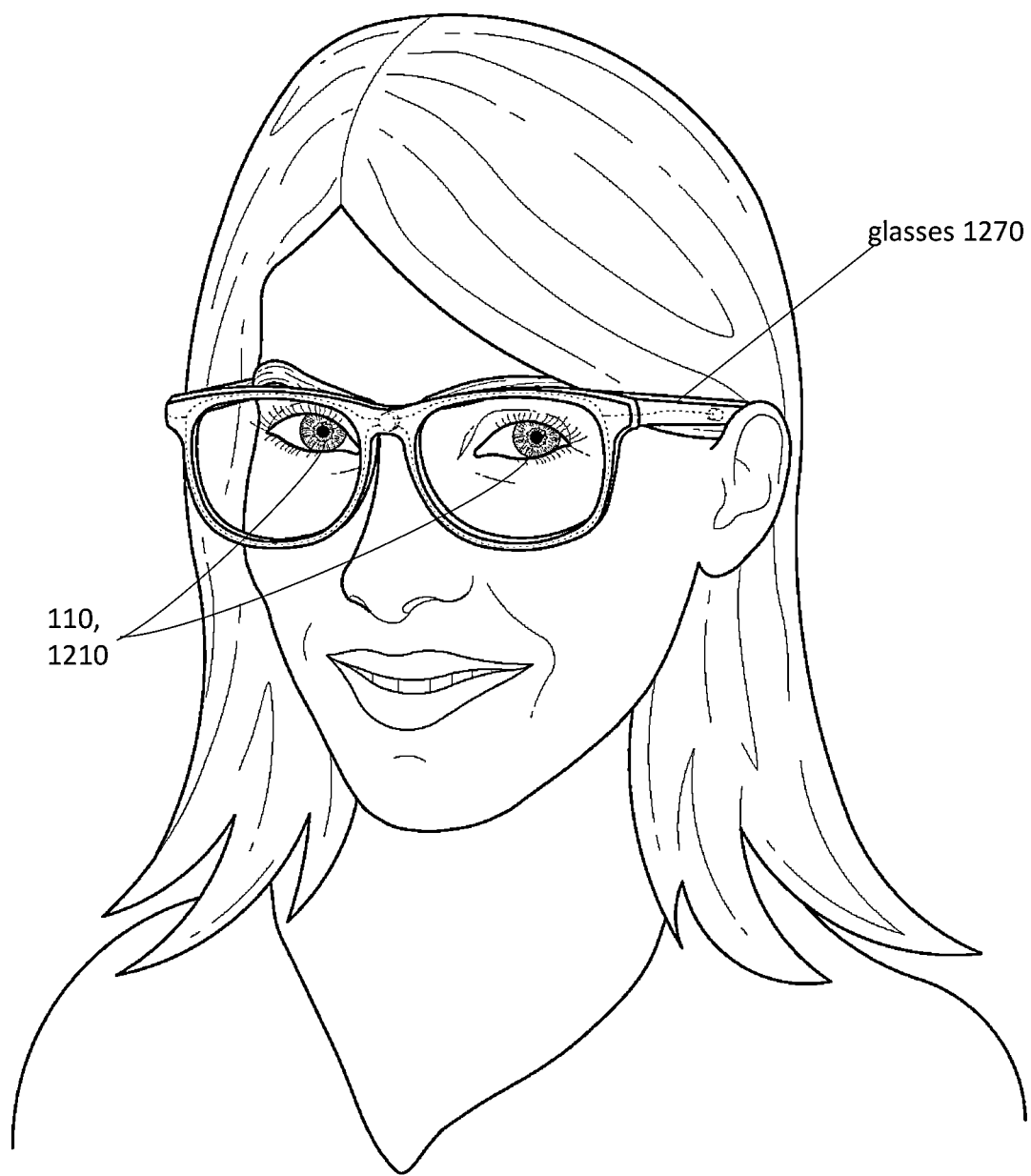
FIG. 12A shows an intraocular femtoprojector used with an eyeglasses accessory and a contact lens-mounted femtoimager.
Figure 12B:
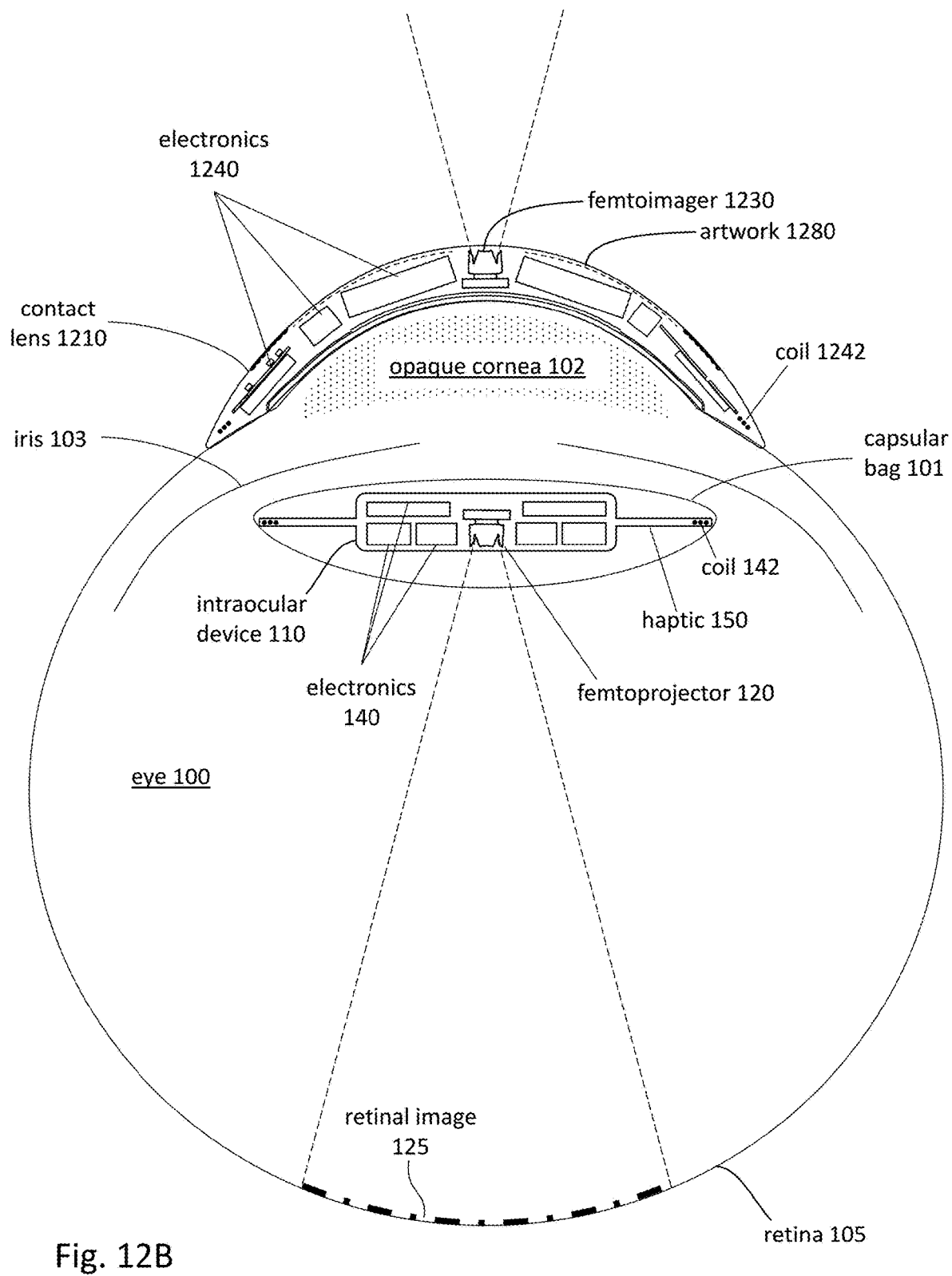
FIG. 12B is a cross-sectional view of the intraocular femtoprojector used with the contact lens-mounted femtoimager.

FIG. 12A shows an electronic intraocular device used with an eyeglasses accessory and an electronic contact lens. FIG. 12B is a cross-sectional view showing the electronic intraocular device and electronic contact lens. In FIG. 12A, the patient has intraocular video femtoprojectors implanted in their eyes, is wearing scleral contact lenses containing femtoimagers, and is wearing glasses that provide electrical power via magnetic induction. The person's appearance is unremarkable as each contact lens includes camouflage artwork 1280 to make the eyeballs appear normal.

The electronic intraocular device 110 is the same as described previously. For example, see FIG. 1. It contains a femtoprojector 120 and electronics 140. It may include microprocessors/controllers, motion sensors (such as accelerometers, gyroscopes and magnetometers), radio or other types of data transceivers including antenna, power circuitry, and batteries and elements for wireless power transfer (e.g., coil 142).

The electronic contact lens 1210 is a scleral contact lens that is worn on the surface of the eye. Contact lenses are usually designed to transmit oxygen to the cornea because a normal cornea has no blood vessels in it. However, when a cornea is vascularized, it may not need as much exposure to ambient air to receive oxygen. In fact, a vascularized cornea may tolerate a contact lens that transmits little or no oxygen for several hours or more.

The contact lens 1210 contains a small imager (femtoimager 1230) and electronics 1240. The femtoimager 1230 captures images of the user's external environment and these images are relayed via a signal path to the femtoprojector 120 for projection onto the user's retina. If the femtoimager 1230 and femtoprojector 120 are optically aligned and the signal path between the two is fast enough, then the femtoprojector 120 will project onto the user's retina the scene that the user would have seen if they did not have corneal damage. In this way, some vision may be restored. The femtoimager 1230 may also operate in non-visible wavelengths: ultraviolet, infrared, etc. These images may then be projected onto the user's retina, thus enhancing the user's vision beyond normal human wavelengths.

Furthermore, both the electronic contact lens 1210 and electronic intraocular device 110 move with the eye and with each other. Therefore, they are auto-aligning, and a person's ability to look around with their natural eye aiming mechanism is preserved. The femtoimager 1230 in the contact lens will automatically point to wherever the user is looking. The femtoprojector 120 in the intraocular device will automatically project an image that appears where the user is looking. This avoids or reduces the need for complex eye tracking components, as may be used with cameras or projectors that do not move with the eye.

The electronic contact lens 1210 may also contain many of the same components as the intraocular device 110: microprocessors/controllers, motion sensors (such as accelerometers, gyroscopes and magnetometers), radio or other types of data transceivers including antenna, power circuitry, and batteries and elements for wireless power transfer (e.g., coil 1242).

The glasses 1270 are an example accessory that can provide various functions. The glasses 1270 may provide power to the contact lens 1210 and/or intraocular device 110, for example through magnetic induction using coils 142 and 1242. In one design, the glasses 1270 include coils of wire surrounding each lens. The coils in the glasses may be connected to a power source such as a battery in the glasses or a battery worn elsewhere on the body and connected to the glasses by wires. When the coils are energized, they transmit power to the contact lens 1210 and intraocular device 110 via magnetic induction. If the optional glasses are not included in the system or not worn, then the contact lenses 1210 may transmit power to the intraocular device 110 via magnetic induction. The glasses and/or contact lenses may also transmit data to the intraocular device by modulating a power signal (e.g. 10-20 MHz carrier) or by a separate radio link (e.g. 1-10 GHz carrier).

The glasses may also contain components that provide a data channel to the electronic contact lens 1210 and/or the electronic intraocular device 110. The glasses 1270 may also contain eye tracking components. Other types of accessories or additional accessory components may be used, and the glasses 1270 may serve as a relay to these other accessory components.

In more detail, FIG. 12B shows a cross sectional view of the contact lens 1210 with embedded femtoimager 1230. FIG. 12B shows an embodiment using a scleral contact lens but the contact lens 1210 does not have to be scleral. The contact lens 1210 preferably has a thickness that is less than two mm. The femtoimager 1230 preferably fits in a 1 mm×1 mm×1 mm volume, or at least within a 2 mm×2 mm×2 mm volume.

The femtoimager 1230 is outward-facing, meaning the femtoimager "looks" away from the eye 100 and captures images of the surrounding environment. The field of view of the femtoimager 1230 may be the same, smaller or larger than a field of view of the user's eye. As shown in more detail below, the femtoimager 1230 includes imaging optics, a sensor array and sensor circuitry. The sensor array may be an array of photodiodes. In some embodiments, the sensor array operates in a visible wavelength band (i.e., ~390 nm to 770 nm). Alternatively or additionally, the sensor array operates in a non-visible wavelength band, such as an infrared (IR) band (i.e., ~750 nm to 120 um) or an ultraviolet band (i.e., <390 nm). For example, the sensor array may be a thermal infrared sensor. In alternate embodiments, an outward-facing imager may be contained in the glasses 1270 instead of in the contact lens.

The sensor circuitry senses and conditions sensor signals produced by the sensor array. In some instances, the output signals produced by the sensor circuitry are analog signals. Alternatively, the sensor circuitry may include analog-to-digital converters (ADC), so that the output signals are digital rather than analog. The sensor circuitry may also have other functions. For example, the sensor circuitry may amplify the sensor signals, convert them from current to voltage signals or filter noise from the sensor signals to improve a signal-to-noise ratio. The sensor circuitry may be implemented as a separate electronics module 1240. Alternatively, it may be implemented as a backplane to the sensor array. Processing of the images captured by the femtoimager may occur outside the eye-mounted components 1210 and 110.

Figure 12C:
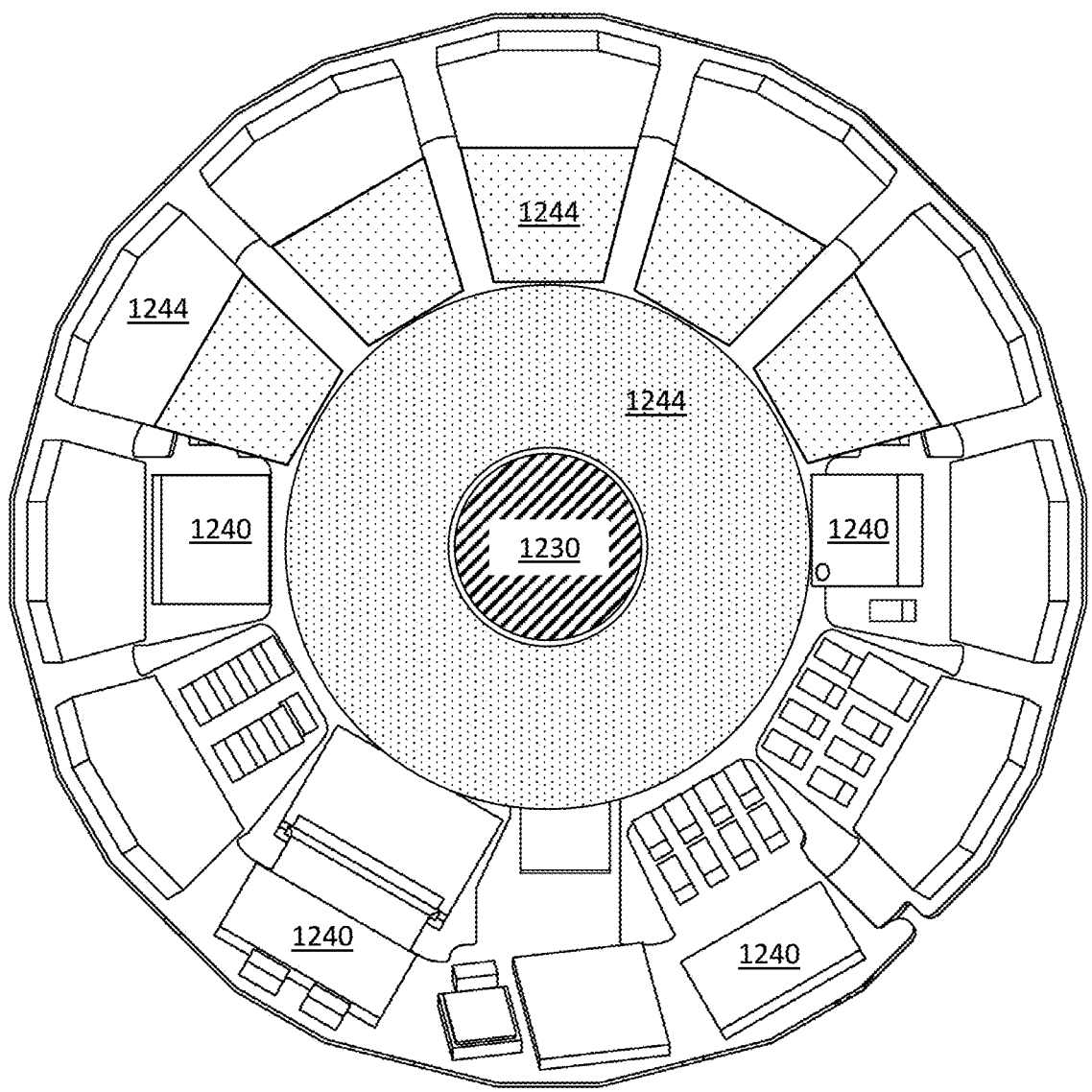
FIG. 12C is a posterior view of an electronics assembly suitable for use in an electronic contact lens.

FIG. 12C is a posterior view of an electronics assembly suitable for use in a contact lens. The electronics assembly is approximately dome-shaped in order to fit into the contact lens. The posterior view of FIG. 12C shows a view from inside the dome. The perimeter of the dome is closer to the viewer and the center of the dome is away from the viewer. The surfaces shown in FIG. 12C face towards the wearer's eye.

The electronic components include electronic circuits 1240, batteries 1244 and femtoimager 1230. Electronic circuits 1240 may include microprocessors/controllers, motion sensors, radio or other types of data transceivers including antenna, power circuitry, and elements for wireless power transfer. The components are mounted on a flexible circuit board that is folded into a shape that fits into a contact lens. If the patient had normal vision, the electronics assembly would have a clear aperture to allow light to pass through to the patient's retina for normal sight. However, in FIG. 12C, the electromechanical bus on which components are mounted may fill most of the area of the contact lens. There is no need to keep a central portion of the assembly clear if the patient's cornea is opaque, and the contact lens may be opaque to provide a darker background for the femtoprojector images, so long as it does not block the femtoimager. The additional space in the contact lens may be used to contain more batteries to allow the system to operate for a longer time without any external source of power. It may also be used to contain additional circuitry or larger components. The femtoimager may be as large as a normal pupil, for example.

In this particular design, the flexible circuit board is folded into a shape that has flat facets. Most of the bending occurs at creases between the facets. The electronics are mounted on the flat facets and are overmolded with a polymer. The polymer may be designed to have specific stiffness, dimensional stability, adhesion, and/or moisture sealing properties. The overmolding ensures that each facet remains flat and isolated from the surrounding environment. The electronics may be mounted and overmolded onto the circuit board when it is flat. The circuit board is then bent into a conical shape to fit inside the contact lens. A similar approach may be used for the electronics assembly in the intraocular device, but without requiring bending of the circuit board. Other examples of electronic assemblies are described in U.S. patent application Ser. No. 16/047,737 "Electrical Interconnects within Electronic Contact Lenses" and Ser. No. 16/554,399, "Electronics Assembly for use in Electronic Contact Lenses", which are all incorporated by reference herein.

Figure 13A:
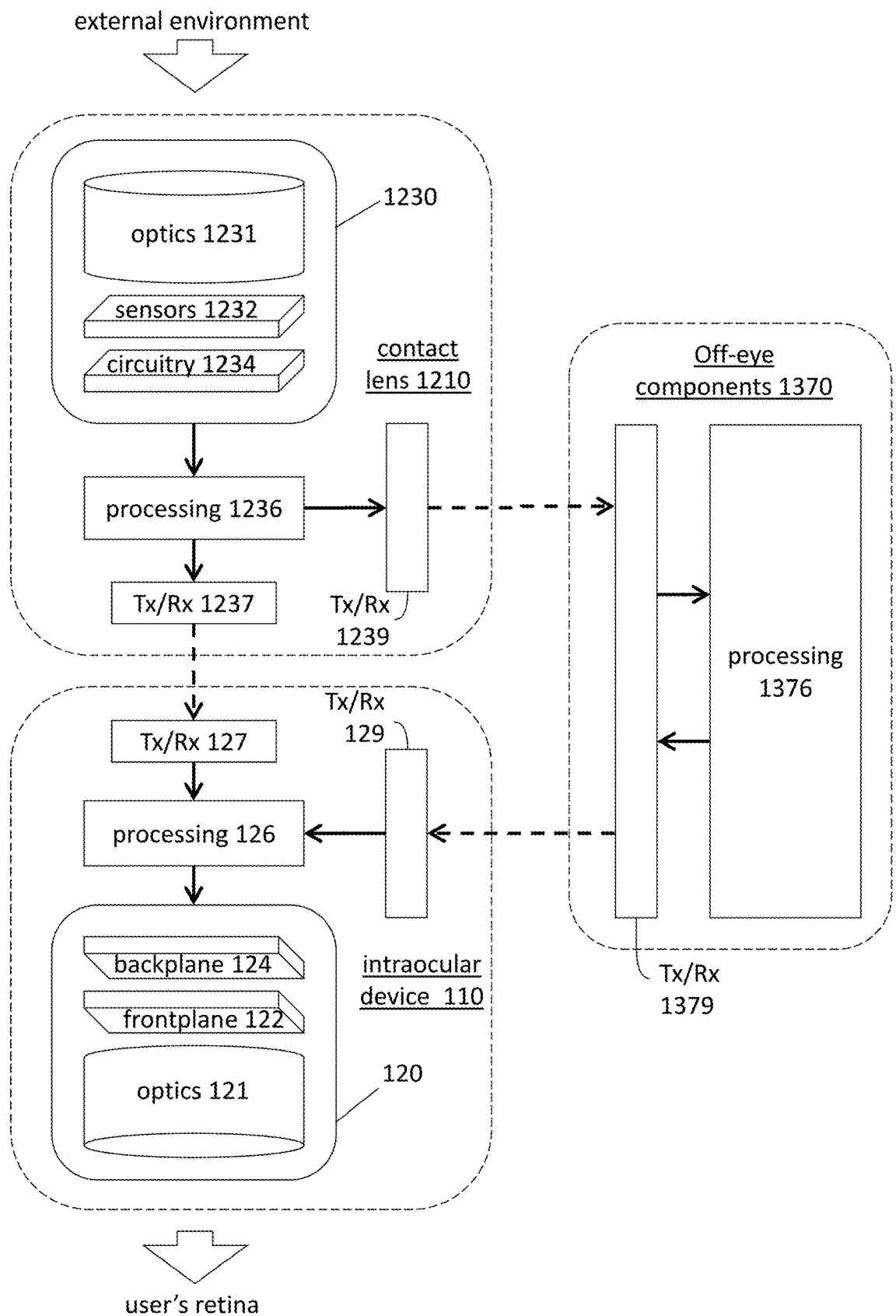
FIGS. 13A-13C are block diagrams of different image signal paths for a system using an eye-mounted femtoimager and intraocular femtoprojector.

FIG. 13A is a block diagram of an image signal path for a system using an electronic contact lens 1210, electronic intraocular device 110 and off-eye components 1370 such as eyeglasses. The image processing pipeline begins with the femtoimager 1230 capturing images of the external environment and ends with the femtoprojector 120 projecting the captured images or processed versions of those images. The femtoimager 1230 includes imaging optics 1231, a sensor array 1232 and a sensor circuitry 1234. The imaging optics 1231 images a portion of the external environment onto the sensor array, which captures the image. The projection optics design of FIG. 9 may be used as imaging optics 1231. Other examples are described in U.S. patent application Ser. No. 16/001,778 "Folded Optical Designs for Eye-Mounted Cameras", Ser. No. 16/034,761 "Advanced Optical Designs for Eye-Mounted Imaging Systems", and Ser. No. 16/895,077 "Advanced Optical Designs for Eye-Mounted Imaging Systems", which are all incorporated by reference herein. The sensor array 1232 may be an array of photodiodes. In some embodiments, the sensor array 1232 operates in a visible wavelength band (i.e., ~390 nm to 770 nm). Alternatively or additionally, the sensor array 1232 operates in a non-visible wavelength band, such as an infrared (IR) band (i.e., ~750 nm to 120 μm) or an ultraviolet band (i.e., <390 nm). For example, the sensor array 1232 may be a thermal infrared sensor.

The sensor circuitry 1234 senses and conditions the sensor signals produced by the sensor array 1232. The sensor circuitry 1234 may include analog-to-digital converters (ADC), so that the output signals are digital rather than analog. The sensor circuitry 1234 may also have other functions. For example, the sensor circuitry 1234 may amplify the sensor signals, convert them from current to voltage signals or filter noise from the sensor signals to improve the signal-to-noise ratio. The sensors 1232 and corresponding circuitry 1234 may be implemented on a single die.

The images signals are sent along signal paths from the sensor circuitry 1234 through optional image processing circuitry 1236/126 to driver circuitry 124 of the femtoprojector 120. In this example, the image processing is performed in part by circuitry 1236 in the contact lens 1210 and in part by circuitry 126 in the intraocular device 110. Partially processed images are transmitted from the contact lens 1210 to the intraocular device 110 via the wireless channel using transmitter 1237 and receiver 127. This channel may be based on inductive coupling, optical or infrared transmission, capacitive coupling, radio frequency transmission (e.g. within the 1-10 GHz band), ultrasound or through-body transmission. The type of transmitter 1237 and receiver 127 depends on the type of communications channel used.

The image processing circuitry 1236/126 may perform various types of image processing on the image data received from the femtoimager 1230. One type of image processing is edge enhancement, where the processing circuitry 1236/126 identifies edge boundaries in the imagery signals and increases a contrast around the identified edge boundaries. Other types of image processing may include contrast or brightness enhancement, blurring, sharpening, and magnification. In some embodiments, the processing circuitry 1236/126 may process images captured by the femtoimager 1230 to generate an overlay.

The femtoprojector 120 projects images inward to the user's retina. The projected images correspond to the images captured by the femtoimager 1230 as processed by the processing circuitry 1236/126. The images projected by the femtoprojector 120 are visible to the user's retina because the femtoprojector operates at a visible wavelength band, regardless of whether the femtoimager 1230 operates in a visible wavelength band or a non-visible wavelength band. The femtoprojector 120 includes driver circuitry 124, an LED (light emitting diode) array 122 and projection optics 121. In one approach, the driver circuitry 124 and LED array 122 are manufactured separately and later bonded together to form electrical connections. Alternately, they can be integrated on a single common substrate.

The driver circuitry 124 receives images from the processing circuitry 1236/126 and converts these to drive signals to drive the LED array 122 (e.g., drive currents for LEDs). In some embodiments, the driver circuitry 124 enhances the images, e.g., by amplifying the imagery signals. To save power, the driver circuitry 124 and LED array 122 may power down when no images are being projected. If the images are clocked data packets, the no signal situation may be detected when there is no clock present, for example if there is no clock signal on clock input pins or if no clock can be recovered from the incoming data stream. Also, the drive signals produced by the driver circuitry 124 may not be persistent. That is, the drive signals cause a corresponding subset of LEDs 122 to produce light, but only when the drive signals are applied. Once the backplane 124 no longer produces those drive signals, those LEDs 122 also cease to produce light.

The LED array 122 contains an array of LEDs that produce light according to the drive signals from the driver circuitry 124, thus generating images corresponding to the images detected by the femtoimager 1230. The array of light emitters 122 can have different geometries. One example geometry is a rectangular array of LEDs. Another example geometry is a hexagonal array of LEDs. The projection optics 121 project light from the LEDs to the retina. Thus, the femtoprojector 120 forms a visual sensation of imagery. The portion of the retina illuminated by the femtoprojector 120 does not change as the user's eye rotates in its socket. In some embodiments, the light from the LEDs are projected onto the retina with pixel resolutions that are higher for pixels projected to the fovea of the retina and lower for other more peripheral sections of the retina.

The femtoimager 1230 is characterized by a line of sight. The line of sight indicates a direction along which the femtoimager 1230 detects imagery. The femtoprojector 120 is characterized by a line of projection, indicating a direction along which the femtoprojector 120 projects corresponding imagery to the user's retina. In some embodiments, the line of sight of the femtoimager 1230 is parallel to the line of projection of the femtoprojector 120. For perfect alignment, the line of projection may also be collinear with the line of sight, although lack of alignment in this respect is less important. The femtoimager 1230 and the femtoprojector 120 may have the same field of view/span of eccentricity and spatial resolution. Span of eccentricity of a femtoprojector is analogous to field of view of a femtoimager. It is the angular extent that appears to be occupied by the image created by the femtoprojector, as measured in the user's external environment.

In FIG. 13A, some processing is also performed by components 1376 outside the contact lens 1210 and intraocular device 110. The components 1376 may be contained in eyeglasses, other types of headgear, belts, armbands, wrist pieces, necklaces, or other types of packs. For example, see U.S. patent application Ser. No. 16/530,949 "Headgear Providing Inductive Coupling to a Contact Lens", which is incorporated by reference herein.

As an example, image processing circuitry 1236 may pre-process the images and image processing circuitry 126 may be configurable to implement different types of image processing, depending on the content of the images captured by the femtoimager. Off-eye components 1370 may be used to analyze the content of the captured images and determine the appropriate type of image processing. Performing these tasks off-eye reduces power consumption by the eye-mounted components (contact lens 1210 and intraocular device 110). The femtoprojector then projects the resulting images onto the user's retina.

Transmitters and receivers 1239, 1379, 129 are used to communicate with the off-eye processing components 1370 for handling more computationally-intensive processing functions. For example, a transmitter 1239 may periodically transmit one or more captured images to the off-eye processing component 1370, which determines a context of the captured images. The receiver 129 receives a corresponding configuration parameter from the off-eye processing component 1370, which is used to configure the functionality of the image processing circuitry 126. By partitioning different types of processing functions between the contact lens circuitry 1236, the off-eye processing components 1376 and the intraocular circuitry 126, the amount of area and power consumed by the eye-mounted circuitry may be reduced. In addition, by separating context determination from the image processing performed on the signal path, the image processing can be performed with lower latency.

In some embodiments, power consumption by the on-eye image processing circuitry may be further reduced by simplifying arithmetic operations, such as by implementing multiplication with left/right bit shifters, implementing subtraction as bit inversion, etc. In addition, to reduce latency, the image processing circuitry may process captured images by streaming rows of the images rather than by storing and processing entire frames of the images.

Figure 13B:
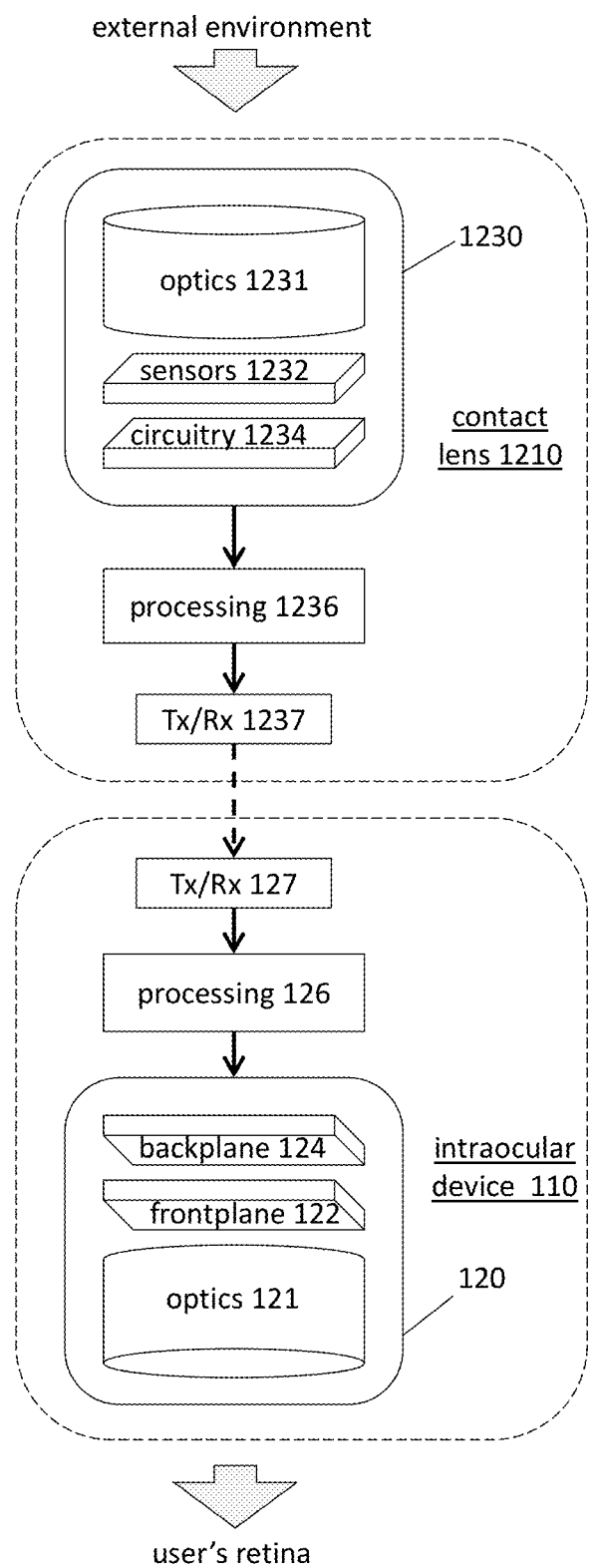
Figure 13C:
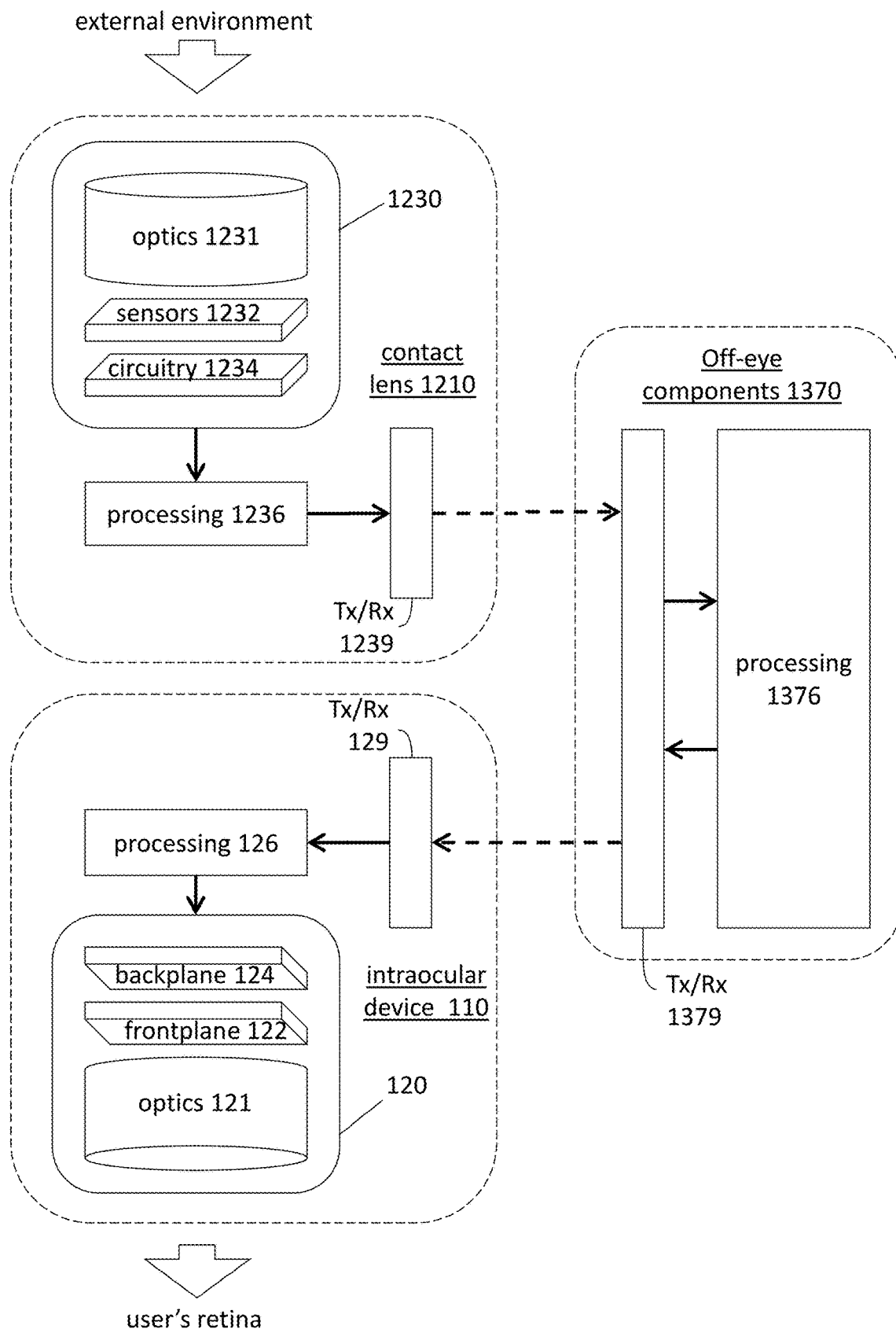

FIGS. 13B and 13C show alternate image processing paths. In FIG. 13B, all of the image processing occurs on-eye, either in the contact lens 1210 or in the intraocular device 110 or both. This image path is simpler in the sense that data communication to off-eye components is not required. In addition, the positions of the contact lens 1210 and intraocular device 110 are fixed relative to each other, so the data transmission channel 1237/127 can be optimized for this fixed geometry. However, power and space are limited in the eye-mounted components 1210, 110, so the image processing is also limited. In FIG. 13A, some of the more compute-intensive processing is shifted to off-eye components, but images are still transferred from the contact lens 1210 to the intraocular device 110. In FIG. 13C, the image path is entirely through off-eye components 1370. Images captured by the femtoimager 1230 are transmitted 1239/1379 off-eye where they are processed 1376, and the resulting images are then transmitted 1379/129 back on-eye for display by the femtoprojector 120.

Many variations and extensions of the technologies described above are possible. Power may be transmitted between any of a contact lens, an intraocular device, glasses or other accessory device via magnetic induction, capacitive coupling, ultrasound, radio waves, infrared light, or through-body channels. Similarly, data may be transmitted between any of a contact lens, an intraocular device, glasses or other accessory device via magnetic induction, capacitive coupling, ultrasound, radio waves, infrared light or through-body channels. Data may be transmitted via modulated carrier frequencies or at baseband. In through-body communication, the human body tissue is the transmission medium. For example, see U.S. patent application Ser. No. 16/523,996, "Through-Body Ocular Communication Devices, Networks, and Methods of Use," which is incorporated by reference herein. Electrodes on the intraocular device or electronic contact lens may be used to detect through-body electrical signals. In some cases power and data may be transmitted via the same channel, e.g. via a modulated ultrasonic carrier. In other cases power and data may be transmitted via different channels, e.g. power transmitted via a through-body channel and data transmitted via capacitive coupling.

Different numbers of femtoprojectors and femtoimagers may be used. The intraocular device may contain multiple femtoprojectors, as described previously. Analogously, the contact lens may also contain multiple femtoimagers. The system may switch between different femtoimagers or may use multiple femtoimagers simultaneously. For example, in the architecture of FIG. 13B, different femtoimagers may be connected to the femtoprojector(s) at different times. Additional cameras in the eyeglasses or located elsewhere may also be used in addition to or in place of the femtoimagers in the contact lens.

The contact lens and/or intraocular device may include eye tracking sensors. Images and/or eye tracking data captured by these eye-mounted components may be used to select portions of high resolution images captured by glasses for display by the intraocular femtoprojector.

Figure 14:
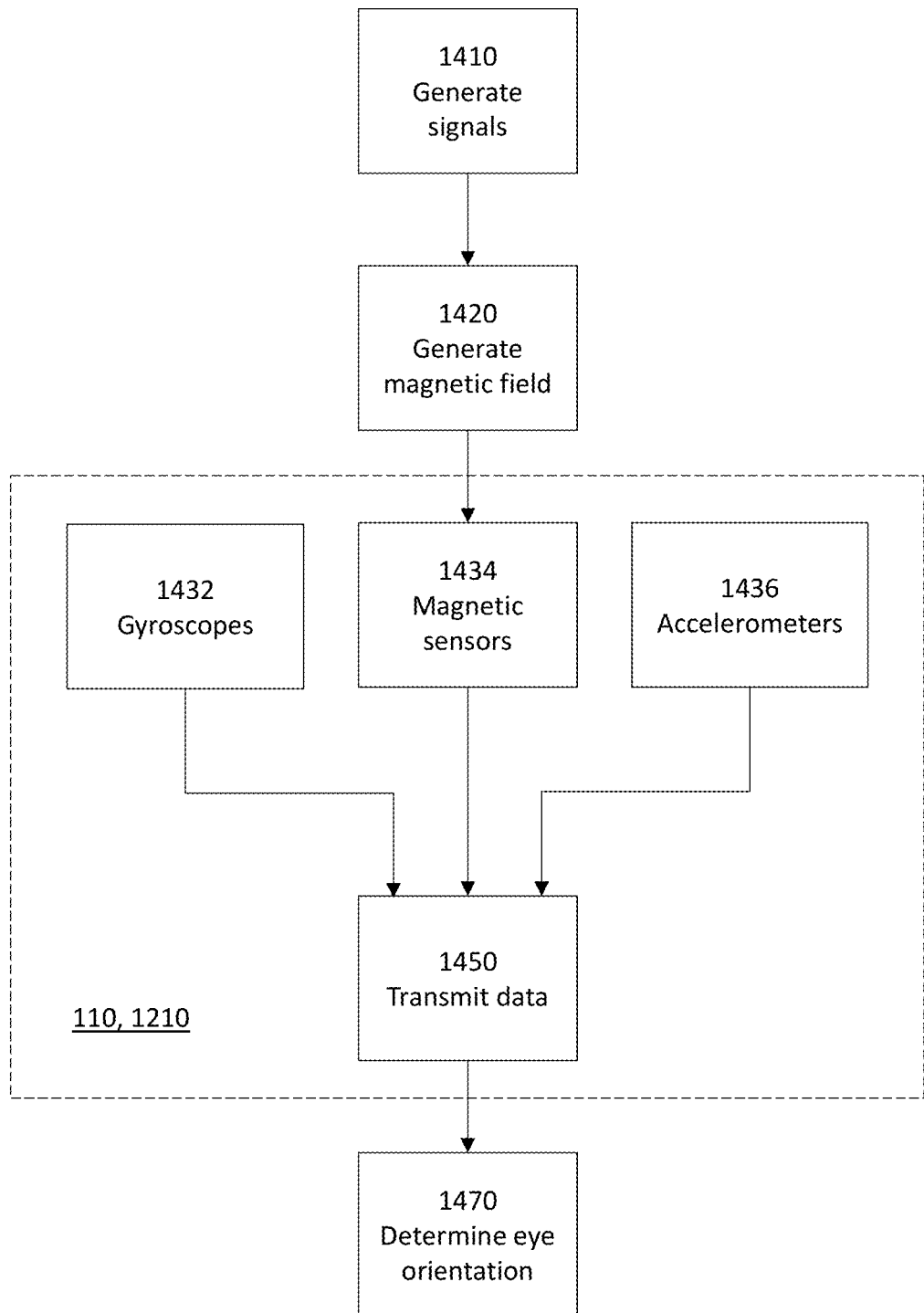
FIG. 14 is a flow diagram for determining the orientation of the eye from measurements of a magnetic field generated by an external device.

FIG. 14 is a flow diagram for determining the orientation of the eye from measurements of a magnetic field generated by an external device, for example an RF magnetic field. The method in FIG. 14 also uses inertial measurements from accelerometers 1436 and gyroscopes 1432. The gyroscopes 1432, magnetic sensors 1434 and accelerometers 1436 are contained in the electronic contact lens 1210, in the electronic intraocular device 110 or distributed between the two. An external device generates 1410 signals for determining the orientation of the eye. For example, DC signals may be generated and converted into AC signals suitable for driving a conductive coil. The AC signals are driven through a coil to generate 1420 a time-varying magnetic field. The external device may include more than one coil and generate more than one magnetic field. In that case, the external device may pre-process 1410 the signals such that each coil's contribution to the magnetic field is distinguishable from the others. For example, time, frequency, phase or code division multiplexing may be used.

Eye tracking sensors on the contact lens and/or intraocular device sense information that may be used to determine the orientation of the eye. In this example, gyroscopes 1432 measure angular velocity, accelerometers 1436 measure acceleration, and magnetic sensors 1434 measure magnetic fields. These measurements are taken on-eye (i.e., within the contact lens or intraocular device), because the corresponding sensors are on-eye. The on-eye devices may compress the measurement data and transmit 1450 it off-eye for processing. Other types of pre-processing may also occur on-eye before transmission off-eye. Examples include smoothing, averaging and filtering of data, data cleaning and outlier checking of data, processing to generate a virtual inertial measurement unit (equivalent of accelerometers plus gyroscope), de-multiplexing and/or identifying magnetic field sources, and calculation of differential or differences over time, such as velocity change, position change, and orientation change. Other pre-processing steps are also possible. In some cases, the eye tracking computations may be performed on-eye rather than entirely off-eye.

An external device receives the measurements and determines 1470 the orientation of the eye. The device may also perform additional, or similar, processing functions on the measurement data before determining the orientation of the eye (e.g., de-multiplexing magnetic field measurements). Various combinations of data from the sensors may be used determine 1470 the orientation of the eye. For example, acceleration and magnetic field measurements may be used; or angular velocity, acceleration, and magnetic field measurements may be used. In some embodiments, only magnetic field measurements are used. Additionally, Kalman filtering may be used to track the eye using various combinations of measurements. For further examples, see U.S. patent application Ser. No. 16/005,379 "Contact Lens-Based Eye Tracking" and U.S. Ser. No. 16/839,066 "Contact Lens-Based Eye Tracking Using Magnetic Fields", which are all incorporated by reference herein.

Figure 15:
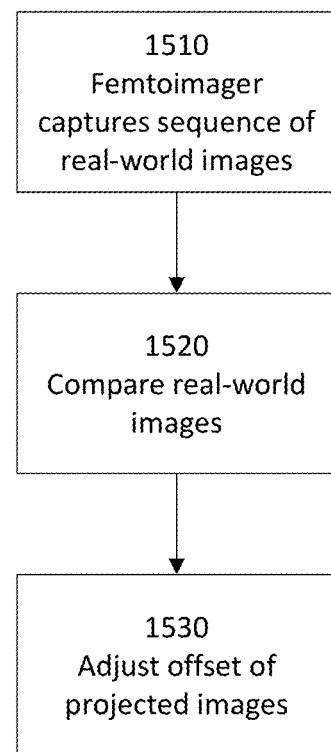
FIG. 15 is a flow diagram of image-based eye tracking.

FIG. 15 is a flow diagram of image-based eye tracking. The method shown in FIG. 15 stabilizes the virtual images projected by the femtoprojector. The initial position of the virtual image may be determined based on other data, such as from inertial motion sensors. Regardless of how it is initially placed, the virtual image is then stabilized relative to the external environment and its initial placement using the method of FIG. 15. As described previously, the femtoprojector and femtoimager may be aligned and move together. The method of FIG. 15 uses the known relation between the femtoprojector and femtoimager to stabilize the virtual image based on images of the environment captured by the femtoimager.

In FIG. 15, the outward-facing femtoimager captures 1510 a sequence of images (frames) of the external environment. The real-world frames are compared 1520, and the position of the virtual image produced by the femtoprojector is adjusted 1530 based on the comparison. Because the spatial relation of the femtoprojector and the femtoimager are known, the amount of shift of the femtoprojector can also be calculated from the shift in the real-world frames captured by the femtoimager. The source of the virtual image may then be offset by a corresponding amount on the LED array to compensate. The offset may be a translation and/or rotation.

Different approaches may be used to implement step 1520. One approach is based on tracking movement of a template within the sequence of real-world images. A "template" is a region of pixels within a real-world frame, for example a 100×100 pixel region with some amount of detail. The template is tracked across frames, so the template should have distinctive characteristics that facilitate this tracking. For example, the template may be selected based on the detail and/or contrast in a region. The size of the template may vary depending on the motion being tracked. Larger templates provide higher confidence in tracking from frame to frame, but require more computational resources and are slower to implement. In addition, if the eye motion is faster, then consecutive frames will have less overlap, so larger templates may lose correlation with previous frames more quickly. When a template approaches the edge of the frame, it may be replaced by another template that is currently closer to the center of the frame. Alternatively, sequential latching may be used where the template is updated every N frames. In one approach, the size of the template is selected based on the speed of the eye motion.

Another approach uses features. Features, such as corners, edges, etc. are extracted from a real-world image. These features are then tracked in the real-world images, thus providing information that may be used to compensate for the unwanted motion of the virtual images from the femtoprojector. For further examples, see U.S. patent application Ser. No. 16/865,079 "Stabilizing Images Produced by Eye-Mounted Displays, Based on Images of the External Environment Captured by Eye-Mounted Imaging Devices", which is incorporated by reference herein.

FIGS. 16-19 illustrate another example of an electronic intraocular device. This example is an electronic capsular tension ring (eCTR). Diabetic retinopathy and age-related macular degeneration are diseases that each year rob hundreds of thousands of people of their eyesight. Although the two diseases are different from each other, they are both diseases of the retina which is the interior lining of the back of the eyeball where images focused by the cornea and crystalline lens are detected. The earlier an eye problem is detected, the more likely it is to be successfully treated or managed. The prevalence of retinal diseases is low, but the consequence of not catching them early on is potentially severe. Unfortunately most people are not aware of the risks and tradeoffs of not undergoing routine eye exams and skip them entirely, especially if they don't need glasses to see clearly. The electronic capsular tension ring (eCTR) described below may be used to monitor retinal health with shorter time intervals between exams and less hassle for patients.

An electronic capsular tension ring (eCTR) is a device that may be implanted in the capsular bag of a person's eyeball similarly to the way that a conventional capsular tension ring is implanted during cataract surgery. In one embodiment, the eCTR contains a femtoimager that captures images of the retina. The images may be examined by a doctor to screen for the onset of retinal diseases.

When a patient wants to take a picture of her retina and send it to her doctor, she wears glasses for a short time. The glasses transmit electrical power to the eCTR inductively and receive image data from the eCTR the same way. The glasses then connect to the internet to send the images. For example, the glasses may appear as a Bluetooth accessory to a smartphone.

When the patient removes the glasses, over-the-air power to the eCTR is cut off and it remains in the eyeball doing nothing until the next time the patient wants to take a picture. A doctor's instructions to the patient may be a simple as: (a) turn on the glasses, connect them to your smartphone via Bluetooth, and wear them; (b) open the retinal health check app on your smartphone and press "capture image"; (c) when the app indicates success (usually within a few seconds), press "send to doctor"; (d) turn off the glasses and put them away until next time. If the doctor hasn't received data from the patient recently, then she may send a reminder email.

Furthermore, a doctor may not be necessary as an artificial intelligence (AI) image analysis system may be trained to examine images automatically. The AI system may be able to identify subtle indications of retinal diseases long before a human doctor, or in a less ambitious system it may be able to flag problems for a human doctor to review without producing an estimate of what the problem is.

Figure 16:
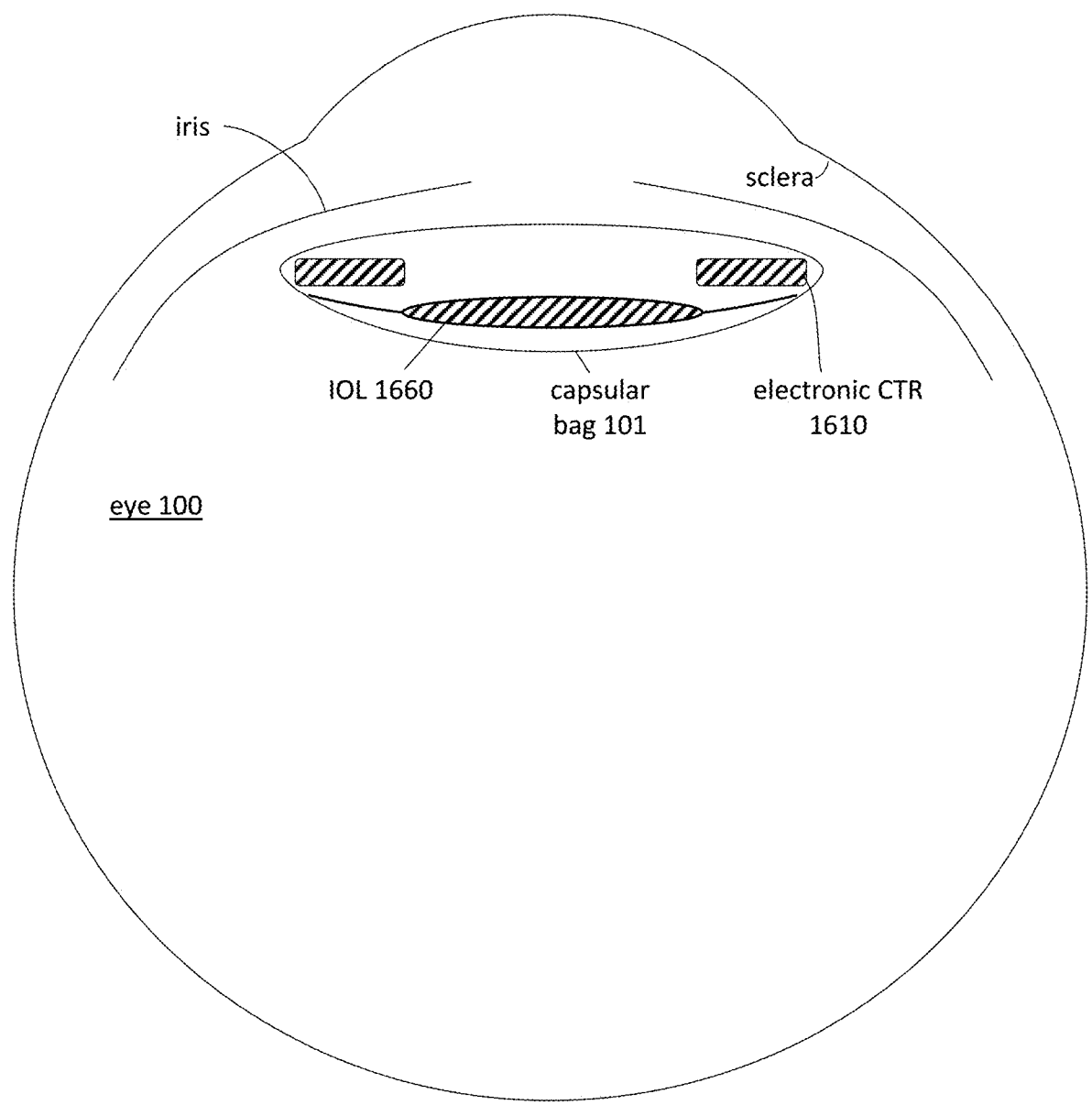
FIG. 16 is a cross-sectional diagram of an eye which has both a conventional intraocular lens (IOL) and an electronic capsular tension ring implanted in the capsular bag.

The eCTR is compatible with both natural crystalline lenses and artificial intraocular lenses (IOLs). FIG. 16 is a cross-sectional diagram of an eye 100 which has both a conventional IOL 1660 and an eCTR 1610 implanted in the capsular bag 101. In the figure, the eCTR 1610 is placed anterior to the IOL 1660. While this placement is preferred, it is not required. Placement of the eCTR posterior to an IOL or natural crystalline lens is possible. The eCTR 1610 is shaped like a segment of an annular ring. In FIG. 16, the plane of the cross section is indicated by cross hatching so the optical lens of the IOL 1660 appears as an oval and the eCTR 1610 appears as oblong shapes near the edge of the capsular bag. The eCTR does not obscure the IOL (or a natural crystalline lens) or prevent light from passing through it. Therefore the eCTR does not affect a patient's vision.

Figure 17:
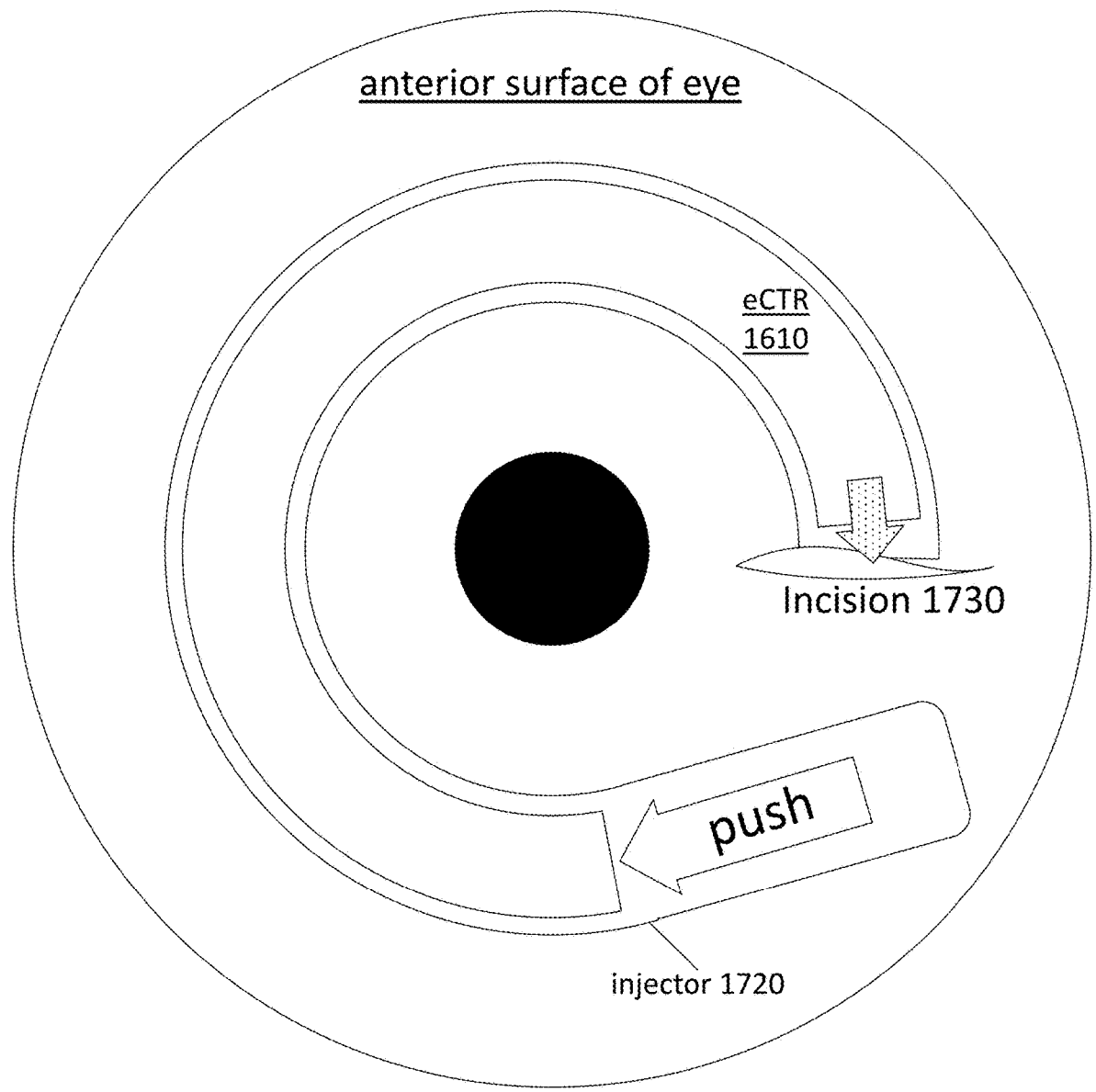
FIG. 17 shows an injector inserting an electronic capsular tension ring into an eyeball through an incision.

An eCTR may be inserted into the capsular bag with an injector 1720, similar to how an IOL is inserted with an injector. FIG. 17 shows an injector 1720 inserting an electronic capsular tension ring 1610 into an eyeball through an incision 1730. The injector 1720 shown in FIG. 17 is a hollow, semi-rigid structure. The part of the injector where the eCTR 1610 is stored prior to launching it into the eye is shaped like a segment of an annular ring. This allows the eCTR to maintain its curved, planar shape before, during and after insertion through a small incision in the eye. Placement of the eCTR is not critical, but it should be placed such that its femtoimager is not obstructed by the haptics of an IOL if present. An ophthalmologist may observe images captured by the eCTR as it is inserted to check that the images are clear.

Figure 18:
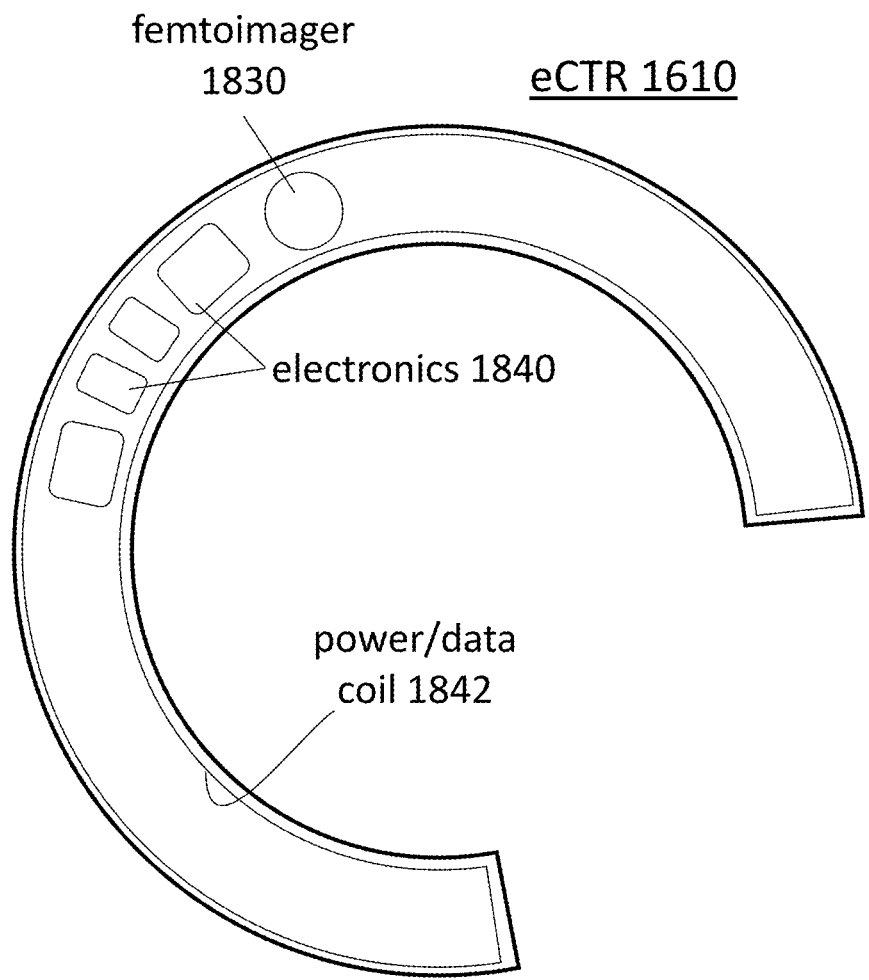
FIG. 18 shows an electronic capsular tension ring including its femtoimager, electronics, and power/data coil.

FIG. 18 shows an electronic capsular tension ring 1610, including its femtoimager 1830, electronics 1840, and power/data coil 1842. The femtoimagers described above may be used in eCTR 1610. The femtoimager 1830 includes an image sensor chip and a femtooptical system that focuses images onto the sensor. The electronics 1840 may include a power and control chip that receives AC power from a power/data coil 1842 and converts it to DC power to drive the femtoimager. The electronics 1840 also include a data radio that transmits data to accessory glasses that are worn during image capture. The electronics 1840 may further include an LED illuminator to illuminate the retina during image capture. The LED may operate at visible or infrared wavelengths, or both. Alternatively, both visible and infrared LEDs may be provided. The eCTR may be constructed on a semi flexible electronic circuit board and hermetically sealed in an inert, biocompatible plastic such as plastics that are used for conventional IOLs and their haptics. The circuit board may be flexible at certain places and stiff in other places. It may be designed to be stiff where chips are bonded to it, as too much flexibility can reduce the reliability of chip-to-board bonds.

Figure 19:
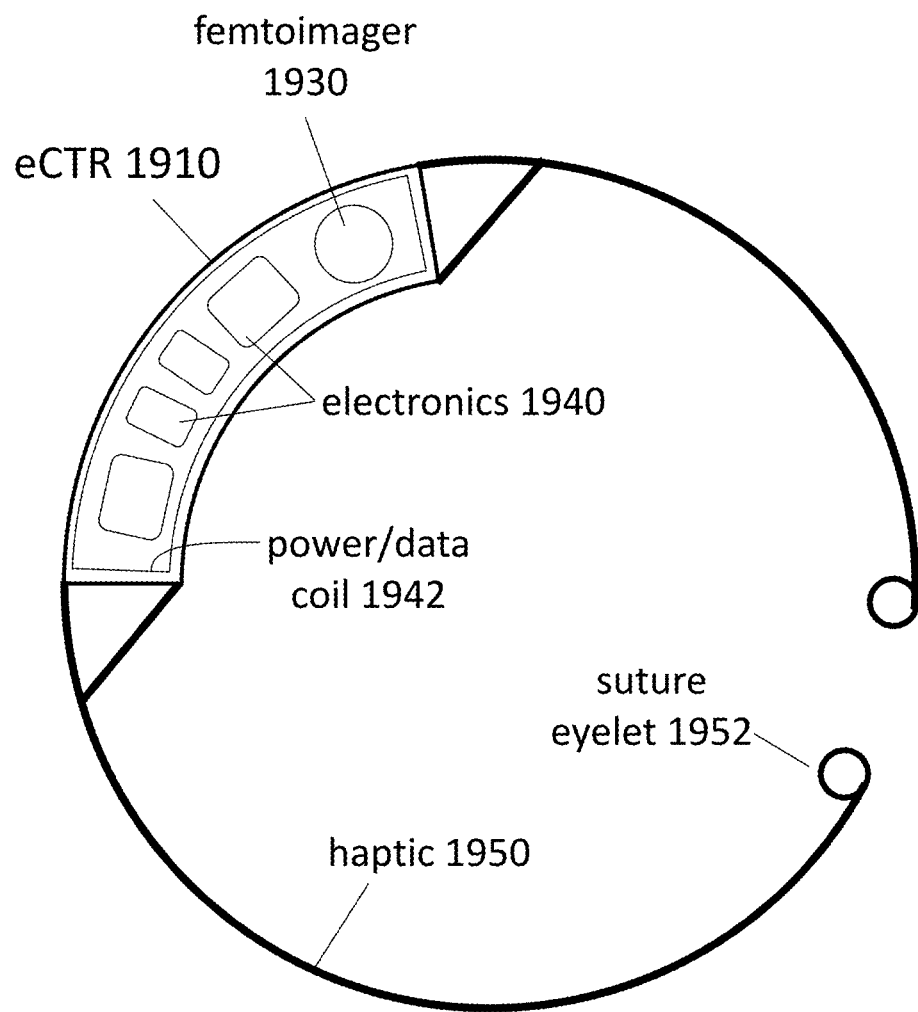
FIG. 19 shows an alternative electronic capsular tension ring.

The eCTR shown in FIG. 18 takes up about nine "clock hours" (i.e. $3\pi/2$ radians) of arc. However, FIG. 19 shows an alternative electronic capsular tension ring 1910 where the electronic payload only occupies about three clock hours (i.e. $\pi/2$ radians) of arc. This design may be thicker than that of FIG. 18. It also includes haptics 1950 and suture eyelet 1952 that are reminiscent of a conventional capsular tension ring as used in its conventional application of controlling zonular instability. In other designs, an eCTR may be in the shape of a complete annular ring.

The eCTR designs shown in FIGS. 18 and 19, and similar designs, do not require precise placement because the field of view of the femtoimager is wide enough to capture at least 30 degrees away from the fovea in all directions. Some femtoimagers may be able to capture images covering up to 60 degrees or more away from the fovea. Images captured by the femtoimager may include a million or more pixels.

As shown previously in FIG. 12A, a person may wear electronic glasses 1270 that communicate with the electronic capsular tension ring. The glasses 1270 contain batteries, a power/data coil (or coils) to send power to, and communicate with the eCTR, and a communication module to connect to an internet accessory such as a smartphone. The glasses may be equipped with an on/off button and a charging port to charge the batteries. The glasses may also upload tuning parameters to the eCTR femtoimager. For example, some femtoimagers may be steerable if the eCTR is inserted in a less than optimal orientation. Other data uploaded includes exposure parameters such as number of images, exposure time, illumination wavelength, etc. Downloaded data may include images captured by the femtoimager and patient ID as examples.

Electronic capsular tension rings provide a convenient system for monitoring retinal health more frequently and potentially more accurately than is now possible. The eCTR may therefore save millions of people from the scourge of deteriorating eyesight.

Alternate embodiments and extensions to the system described above include alternate means of providing power and data to the eCTR. For example, a wireless power and data system may be installed under a patient's pillow or other parts of his sleep ecosystem. In this system glasses are not necessary. The eCTR captures retinal images at night while the patient is sleeping and transmits them automatically for analysis so no patient action is needed. Alternatively an eCTR may harvest and store energy over period of days via thermal, motion or radio-frequency power collection. When enough energy has been accumulated in a battery, capacitor or other storage element, the eCTR captures a retina image and transmits it to a base station in a patient's bedroom. An ultra-low-power-wake-up radio in the eCTR may listen for the base station and initiate image capture and data transfer when the eCTR is near the base station.

Electronic capsular tension rings may also be designed for other applications. For example, with or without a femtoimager, an eCTR may include a pressure sensor for measuring intraocular pressure, a heart rate sensor, a dissolved oxygen concentration sensor, a glucose sensor, and/or other physical or biochemical sensors for monitoring conditions inside an eyeball. Such sensors may be based on microelectromechanical systems and/or chemFET chemical or biochemical detectors. An eCTR may contain gels or biodegradable cross-linked networks for the sustained release of drugs such as pilocarpine for treating glaucoma. Furthermore an eCTR may include a femtoprojector for projecting images onto a patient's retina, thereby providing an augmented reality or virtual reality display.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

What is claimed is:

1. A system for compensating corneal opacity of a patient, the system comprising:
   a contact lens mountable on the patient's eye, the contact lens containing a camera that captures images of a patient's external environment;
   an implantable intraocular device comprising a femtoprojector, wherein the intraocular device is insertable into a capsular bag of the patient's eye and the femtoprojector is positioned to project images onto the patient's retina when the intraocular device is implanted in the patient's eye; and
   a signal path from the camera to the femtoprojector, for processing and transmitting images captured by the camera for projection by the femtoprojector; wherein the contact lens further contains an infrared transmitter, the intraocular device comprises an infrared receiver; and the signal path includes the infrared transmitter, the infrared receiver, and wireless transmission from the infrared transmitter to the infrared receiver.

2. The system of claim 1 wherein a line of sight of the camera is aligned with a line of projection of the femtoprojector.

3. The system of claim 1 wherein the contact lens does not transmit sufficient oxygen to meet safety standards for a person with normal eyesight.

4. The system of claim 1 wherein the contact lens is opaque in a central region and would obstruct a vision of a person with normal eyesight.

5. The system of claim 1 further comprising:
   a plurality of motion sensors that each sense a motion of the patient's eye; wherein the intraocular device comprises at least one of the motion sensors, the contact lens contains at least another of the motion sensors; and
   a processor that receives motion data captured by the plurality of motion sensors and tracks the motion of the patient's eye based on the received motion data.

6. The system of claim 1 further comprising:
power components in the intraocular device and in the contact lens for transmitting power between the intraocular device and the contact lens.

7. The system of claim 1 further comprising:
a plurality of cameras contained in the contact lens, wherein the signal path switchably connects one of the cameras to the femtoprojector.

8. The system of claim 1 wherein the intraocular device has an opaque central region.

9. The system of claim 1 wherein the intraocular device further comprises electronic components located in a central region of the intraocular device, and the electronic components would obstruct a vision of a person with normal eyesight.

10. The system of claim 1 wherein the images projected by the femtoprojector are not compensated for rotation of the patient's eye within the patient's eye socket.

11. The system of claim 1 wherein when the intraocular device is implanted into a patient's eye having a damaged fovea, the femtoprojector is oriented within the intraocular device to project images onto the patient's retina away from the damaged fovea.

12. The system of claim 1 wherein the intraocular device comprises at least two femtoprojectors.

13. The system of claim 12 wherein at least two of the femtoprojectors are redundant.

14. The system of claim 12 wherein at least two of the femtoprojectors project images onto a same area of the patient's retina but are different in at least one of: spatial resolution, and span of eccentricity.

15. The system of claim 12 wherein at least two of the femtoprojectors project images of different colors onto a same area of the patient's retina.

* * * * *